(12) United States Patent
Norris et al.

(10) Patent No.: US 6,271,359 B1
(45) Date of Patent: Aug. 7, 2001

(54) TISSUE-SPECIFIC AND PATHOGEN-SPECIFIC TOXIC AGENTS AND RIBOZYMES

(75) Inventors: James Norris, Mt. Pleasant, SC (US); Gary Clawson, Bethesda, MD (US); Caroline Westwater, Mt. Pleasant, SC (US); David Schofield, Mt. Pleasant, SC (US); Michael Schmidt, Mt. Pleasant, SC (US); Brian Hoel, Charleston, SC (US); Joseph Dolan, Mt. Pleasant, SC (US); Wei-Hua Pan, Hummelstown, PA (US)

(73) Assignees: MUSC Foundation for Research Development, Charleston, SC (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/291,902

(22) Filed: Apr. 14, 1999

(51) Int. Cl.[7] .......................... C07H 21/02; C07H 21/04; C12N 15/00
(52) U.S. Cl. .................. 536/23.1; 536/24.1; 536/24.3; 536/24.5; 435/320.1
(58) Field of Search .................. 435/6, 7.2, 7.32, 435/91.1, 91.31, 91.4, 235, 375, 320.1; 536/23.1, 24.1, 24.3, 24.5; 514/44

(56) References Cited

U.S. PATENT DOCUMENTS 5,166,057  11/1992  Palese et al. .
5,294,533  3/1994  Lupski et al. .

(List continued on next page.)

FOREIGN PATENT DOCUMENTS 0 640 688  3/1995  (EP) .

WO 90/00624  1/1990  (WO) .

(List continued on next page.)

OTHER PUBLICATIONS

Benedict et al. Carcinogenesis 19(7) p1223–30, Jul. 1998.*
Dachs et al. Oncology research 9(6–7) p313–25, 1997.*

(List continued on next page.)

*Primary Examiner*—Remy Yucel
*Assistant Examiner*—M Schmidt
(74) *Attorney, Agent, or Firm*—Pennie & Edmonds LLP

(57) ABSTRACT

The present invention relates to the discovery, identification and characterization of toxic agents which are lethal to pathogens and methods for targeting such toxic agents to a pathogen or pathogen infected cells in order to treat and/or eradicate the infection. In particular, the present invention relates to toxic agents which target bacteria at different stages of the bacterial life cycle, which are delivered alone or in combination to bacteria or bacteria-infected cells. The invention relates to toxic agents which are lethal to diseased cells and methods for targeting such toxic agents to a diseased cell in order to treat and/or eradicate the disease. The present invention relates to promoter elements which are pathogen-specific or tissue-specific and the use of such promoter elements to achieve pathogen-specific or tissue-specific expression of the toxic agent(s) and/or ribozyme(s) of the present invention. Specifically, the invention relates to the delivery of one or more toxic gene products, antisense RNAs, or ribozymes, or combination thereof. The invention provides a novel system by which multiple pathogenic targets may be simultaneously targeted to cause the death of a pathogen, or cell infected with a pathogen. Further, the invention has important implications in the eradication of drug-resistant bacterium and bacterial pathogens. The invention provides a novel system by which multiple targets may be simultaneously targeted to cause the death of a diseased cell. The invention also has important implications in the eradication of drug-resistant pathogens and drug-resistant diseased cells (such as cancer cells).

8 Claims, 5 Drawing Sheets

U.S. PATENT DOCUMENTS

| | | |
|---|---|---|
| 5,436,330 | 7/1995 | Taira et al. . |
| 5,500,357 | 3/1996 | Taira et al. . |
| 5,578,473 | 11/1996 | Palese et al. . |
| 5,670,488 | 9/1997 | Gregory et al. . |
| 5,824,519 | 10/1998 | Norris et al. . |

FOREIGN PATENT DOCUMENTS

| | | |
|---|---|---|
| WO 92/10590 | 6/1992 | (WO) . |
| WO 94/03594 | 2/1994 | (WO) . |
| WO 95/07923 | 3/1995 | (WO) . |
| WO 97/17433 | 5/1997 | (WO) . |
| WO 97/17458 | 5/1997 | (WO) . |
| WO 98/17815 | 4/1998 | (WO) . |
| WO 98/17816 | 4/1998 | (WO) . |
| WO 98/17817 | 4/1998 | (WO) . |
| WO 98/24925 | 6/1998 | (WO) . |
| WO 99/67400 | 12/1999 | (WO) . |

OTHER PUBLICATIONS

Branch, TIBS 23, pp 45–50, Feb. 1998.*

Flanagan et al., Nature Biotech 17: 48–52 Jan. 1999.*

Anderson, Nature 392/Supp. : 25–30, Apr. 1998.*

U.S. application No. 09/319,395, Norris et al.

U.S. application No. 09/338,942, Norris et al.

Bassford et al., 1991, "The Primary Pathway of Protein Export in E.Coli", Cell. 65:789–96 30:367–368.

Bertrand et al., 1994, "Can hammerhead ribozymes be efficient tools to inactivate gene function?", Nucleic Acids Resonant. 22(3) :293–300.

Bouche et al., 1975 "dnaG gene product, a rifampicin resistant RNA polymerase, initiates the conversion of a single stranded coliphage DNA to its duplex replicative form", J. Biol. Chem. 250:5995–6001.

Castanotto et al., 1994, "Antisense Catalytic RNAs as Therapeutic Agents", Adv. in Pharmacol. 25:289–317.

Christoffersen et al., 1995, "Ribozymes as human therapeutic agents", J. Med. Chem. 38(12):2023–37.

Clawson GA, et al., 1996, "Focal altered compartmentation of repetitive B2 (Alu–like) sequences in rat liver following hepatocarcinogen exposure", Cell Growth Differ. 7(5):635–46.

Colberre–Garapin, et al., 1981, "A new dominant hybrid selective marker for higher eukaryotic cells", J Mol Biol 150(1):1–1.

Felgner et al., 1987, "Lipofection: a highly efficient, lipid–mediated DNA–transfection procedure", PNAS 84:7413.

Gewirtz et al., 1996, "Facilitating oligonucleotide delivery: helping antisense deliver on its promise", PNAS 93:3161–3163.

Greenberg et al., 1994, "The rat probasin gene promoter directs hormonally and developmentally regulated expression of a heterologous gene specifically to the prostate in transgenic mice", Mol. Endo.8(2):230–239.

Haseloff et al., 1988, "Simple RNA enzymes with new and highly specific endoribonuclease activities",Nature 334:585–91.

Inokuchi et al., 1994, "A hammerhead ribozyme inhibits the proliferation of an RNA coliphage SP in *Escherichia coli*", J. Biol. Chem. 269(15):11361–6.

Koizumi et al., 1989, "Design RNA enzymes distinguishing a single base mutation in RNA", Nucl. Acids Res. 17(17):7059–71.

Lehnherr H, et al., 1993, "Plasmid addiction genes of bacteriophage P1: doc, which causes cell death on curing of prophage, and phd, which prevents host death when prophage is retained", J. Mol. Biol. 233:414–28.

Major et al., 1991, "The combination of symbolic and numerical computation for three–dimensional modeling of RNA", Science 253:1255–1260.

Marians K.J., 1996, Replication Fork Propagation, p. 749–763. In F.C. Neidhardt (ed.), *Escherichia coli* and Salmonella: Cellular and Molecular Biology, 2nd ed, vol. 1. American Society for Microbiology, Washington, DC.

Merril et al., 1996, "Long–circulating bacteriophage as antibacterial agents", PNAS 93(8):3188–92.

Meyer, et al., 1991, "Search for a putative scrapie genome in purified prion fractions reveals a paucity of nucleic acids", J. Gen. Virol. 72:1031–1038.

Miller et al., 1997, "Progress in transcriptionally targeted and regulatable vectors for genetic therapy", Hum. Gene Ther. 8:803–815.

Nicolau et al., 1987, "Liposomes as carriers for in vivo gene transfer and expression", Methods Enzymol. 149:157.

Ohkawa et al., 1992, "Activities of HIV–RNA targetter ribozymes transcribed from a 'shot–gun' type ribozyme–t-rimming plasmid", Nuc. Acids Symposium Ser.

Ohme–Takagi, 1990, "In vivo RNA transcript–releasing plasmid possessing a universal pseudo–terminator by means of artificial ribozymes", Nucleic Acids Symp Ser. 1990;(22):49–50.

Pace N. & Smith D., 1990, "Ribonuclease P: function and variation", J. Biol. Chem. 256(7):3587–90.

Palese et al., 1996, "Negative–strand RNA viruses: genetic engineering and applications", PNAS 93:11354–11358.

Poulsen, L., et al., 1991, "The gef gene from *Escherichia coli* is regulated at the level of translation", Mol. Microbiol. 5:1639–48.

Schmidt et al., 1991, "Regulation of *Escherichia coli* secA mRNA translation by a secretion–responsive element", J. Bacteriol. 173(20):6605–11.

Schmidt M & Delihas N., 1995 "micF RNA is a substrate for RNase E", FEMS Microbiol Lett. 15;133(3):209–13.

Slopek, S. et al., 1987, "Results of bacteriophage treatment of suppurative bacterial infections in the years", Arch. Immunol. Ther. Exp. (Warsz) 35:569–583.

Soothill JS., "Treatment of experimental infections of mice with bacteriophages", J Med Microbiol. Oct. 1992; 37(4):258–61.

Sternberg N., 1987, "Recognition and cleavage of the bacteriophage P1 packaging site (pac) II. Functional limits of pac and location of pac cleavage termini", J Mol Biol. Apr. 5, 1987;194(3):469–79.

Stull et al., 1995 "Antigene, ribozyme and aptamer nucleic acids drugs: progress and prospects", Pharm. Res. 12(4):465–483.

Sullivan et al., 1994 "Development of ribozymes for gene therapy", J. Investigative Dermatol. 103:85S–95S.

Taira et al., 1991, "Construction of a novel RNA–transcript–trimming plasmid which can be used both in vitro in place of run–off and (G)–free transcriptions and in vivo as multi–sequences transcription vectors", Nuc. Acids Res. 19(9):5125–5130.

Taira et al., "Construction of several kinds of ribozymes their reactivities and utitilities, Gene Regulation, Biology of Antisense RNA and DNA" p35–54.

Taira et al., 1990, "Construction of a novel artificial–ribozyme–releasing–plasmid", Protein Eng. 3(8):733–737.

Templeton et al., 1997, "Improved DNA: liposome complexes for increased systemic delivery and gene expression", Nature Biotechnol. 15:647–652.

Uhlenbeck. O.C., 1987, "A small catalytic oligoribonucleotide", Nature 328(6131):59.

Usman et al., 1996, "Design, synthesis, and function of therapeutic hammerhead ribozymes", Nuc. Acids Biol. 10:243–264.

Vieweg et al., 1995, "Efficient gene transfer with adeno–associated virus–based plasmids complexed to cationic liposomes for gene therapy of human prostate cancer", Cancer Res. 55:2366–2372.

Wigler et al., 1977, "Transfer of purified herpes virus thymidine kinase gene to cultured mouse cells", Cell 11:223.

Whitton J. L., 1994, "Antisense Treatment of Viral Infection", Adv. in Virus Res. 44.

Wigler, et al., 1980, "Transformation of mammalian cells with an amplifiable dominant–acting gene", Proc. Natl. Acad. Sci. USA 77:3567.

Yuyama et al., 1992, "Construction of a T–RNA–embedded–ribozyme trimming plasmid", Biochem. Biophys. Res. Comm. 186(3):1271–1279.

Zhou et al., 1996, "Expression of hammerhead ribozymes by retroviral vectors to inhibit HIV–1 replication: comparison of RNA levels and viral inhibition", Antisense & Nucleic Acid Drug Development 6:17–24.

* cited by examiner

5'-GATCCTCAGAAAATTATTTTAAATTTCCAATTGACATTGTGAGCGGATAACAATATAATGTGGA

UP ELEMENT    -35 ELEMENT    Lac OPERATOR    -10 ELEMENT

FIG.1A

5' AGAAAGCAAAAATAAATGCTTGACACTGTAGCGGGAAGGCCGTATA
ATGGAATTGTGAGCGGATAACAATTCACA 3'

FIG.1B

5'-CAGGCGACAGGTATAGTTTCTCTCCGATTGTGCCTGTCGCCTGC

TISSUE-SPECIFIC AND PATHOGEN-SPECIFIC TOXIC AGENTS AND RIBOZYMES

1. INTRODUCTION

The present invention relates to the discovery, identification and characterization of toxic agents which are lethal to pathogens and methods for targeting such toxic agents to a pathogen or pathogen infected cells in order to treat and/or eradicate the infection. In particular, the present invention relates to toxic agents which target bacteria at different stages of the bacterial life cycle, which are delivered alone or in combination to bacteria or bacteria-infected cells. The invention relates to toxic agents which are lethal to diseased cells and methods for targeting such toxic agents to a diseased cell in order to treat and/or eradicate the disease. The present invention relates to promoter elements which are pathogen-specific. The invention relates to promoter elements which are used to achieve pathogen-specific expression of the toxic agent(s) and/or ribozyme(s) of the present invention. The present invention relates to promoter elements which are tissue-specific. The invention relates to promoter elements which are used to achieve tissue-specific expression of the toxic agent(s) and/or ribozyme(s) of the present invention. Specifically, the invention relates to the delivery of one or more toxic gene products, antisense RNAs, or ribozymes, or combination thereof. The invention provides a novel system by which multiple pathogenic targets may be simultaneously targeted to cause the death of a pathogen, or cell infected with a pathogen. Further, the invention has important implications in the eradication of drug-resistant bacterium and bacterial pathogens The invention provides a novel system by which multiple targets may be simultaneously targeted to cause the death of a diseased cell. The invention also has important implications in the eradication of drug-resistant pathogens and drug-resistant diseased cells (such as cancer cells).

2. BACKGROUND

2.1. Antimicrobial Agents

Infectious diseases sicken or kill millions of people each year. Numerous antimicrobial therapies have been designed to target one or several infectious agents. These therapies show varying degrees of success in eradicating infection. However, the failure of many of these therapies to target specific infectious agents has lead to overuse or inappropriate use of the therapies, which in turn has lead to the development of drug resistant microbes. The development of drug resistance in many infectious agents has reduced the efficacy and increased the risk of using the traditional antimicrobial therapies.

Additionally, a majority of the art has focused on antibacterial agents which target proteins or molecules essential for viability of the bacterium. For example, many antibacterial agents act to disrupt the bacterial cell wall, or target an enzyme required in the cell wall synthesis pathway. However, there is need in the art for novel molecules and novel combinations of molecules that can act as lethal agents in bacteria and which may be delivered to a bacterial pathogen, without causing toxicity to the infected host. The present invention provides such novel products which may be used as toxic agents against pathogens such as bacteria.

2.2. Antisense

Antisense technology seeks to use RNA molecules which are complementary to (or antisense to) a cellular RNA, for the purpose of inhibiting a cellular RNA from being translated into the encoded protein. In this way, the expression of a specific protein is targeted for down regulation. However, a large number of difficulties exist in the art surrounding antisense technology. Commonly, delivery of an exogenous antisense molecule to the target cell is difficult or impossible to achieve. Further, antisense molecules do not consistently lead to a decrease in protein expression. For example, it has been shown that the expression of antisense RNA in transgenic mice did not invariably lead to a reduction in target RNA molecules, and when reduction in target RNA molecules did occur, it was not predictably paralleled by a reduction in protein. Even when protein levels were reduced sometimes no biological effect was detected (Whitton, J. Lindsay "Antisense Treatment of Viral Infection" *Adv. in Virus Res.* Vol. 44, 1994). Thus, there is a need in the art for a delivery system in which antisense molecules may be efficiently delivered to a target cell such as a bacterial pathogen.

2.3. Ribozymes

A ribozyme is a catalytic RNA molecule that cleaves RNA in a sequence specific manner. The use of ribozymes as potential gene regulators in mammalian cells and antiviral agents has been suggested, but are subject to serious questions regarding technical feasibility. For example, there are differences regarding how ribozymes can be introduced to target cells. In the case of eukaryotic cells, questions exist as to how ribozymes can be directed to the same subcellular compartments as their target RNAs. Other questions concern the effects of target RNA secondary structure on ribozyme activity. The art has not been successful in definitively answering these questions.

Furthermore, because ribozymes are a form of antisense technology, the problems encountered in applying antisense technology to disease treatment are also encountered in the use of ribozyme technology.

The experience in the art suggests that it is also not clear whether ribozymes work best when associated with only short non-specific flanking sequences, or when embedded in an unrelated larger RNA molecule (Whitton, 1994 supra). At present, sufficient data are not available, either in vitro or in cell culture to allow systematic comparison of the transactivities of free ribozymes with their embedded equivalents.

Another key technical concern in the use of ribozymes as antimicrobial agents is that the ribozyme must be introduced into and expressed by the targeted microbe so that the ribozyme(s) can cleave the targeted RNA(s) inside the microorganism. A second important concern is the tight coupling of transcription and translation in microorganisms which can prevent binding to and cleavage of the bacterial RNA targets. Additionally, bacterial RNAs often have a shorter half life than eukaryotic RNAs, thus lessening the time in which to target a bacterial RNA. The invention described herein addresses these concerns.

3. SUMMARY OF THE INVENTION

The present invention relates to toxic agents and methods for specifically targeting toxic agents to bacteria or bacteria-infected cells or other pathogens. Toxic agents of the present invention are directed to one or more targets and thus can be used alone or in combination to eradicate bacteria. Specifically, the invention relates to the delivery of one or more toxic proteins, antisense RNAs, multi-ribozymes, or combination thereof, to a cell, tissue, or subject containing an infectious bacteria or pathogen in order to eradicate such bacteria or pathogen.

In one embodiment, the invention relates to toxic agents which specifically target gene products essential for the survival or life cycle of a pathogen (such as replication, packaging etc). In one embodiment, the present invention relates to naturally occurring addiction system toxins which have been modified to be expressed in the absence of the addiction system antidote. In another embodiment, the present invention relates to naturally occurring addiction system toxins which have been modified to be expressed at higher levels than the addiction system antidote. In one example is an addiction system toxin (e.g., Doc) is used as a toxic agent and is uncoupled from its antidote. The invention also relates to antisense RNAs which target essential nucleotide sequences, such as DicF1 or a DicF1-like antisense molecule that specifically target a nucleotide sequence which encodes a protein essential for replication or survival. Further, the invention relates to modified antisense structures with increased stability to act as lethal agents when expressed in bacteria. The invention also relates to toxic sense molecules designed to target essential antisense molecules.

The present invention relates to promoter elements which are pathogen-specific. The invention relates to promoter elements which are used to achieve pathogen-specific expression of the toxic agents of the present invention. The present invention relates to promoter elements which are tissue-specific. The invention relates to promoter elements which are used to achieve tissue-specific expression of the toxic agents of the present invention.

The present invention also relates to multi-ribozymes and their use to target RNA in a tissue-specific or pathogen-specific manner for the treatment of disease such as bacterial infection. The invention provides multi-ribozymes which comprise a cassette including, an enhanced 5' and 3' autocatalytically cleaving ribozyme sequence. The invention provides multi-ribozymes which comprise a cassette including, an enhanced 5' and 3' autocatalytically cleaving ribozyme sequence which are cis-acting and act to release an internal toxic agent or trans-acting ribozyme. The invention provides multi-ribozymes containing one or more internal trans-acting ribozyme. Trans-acting ribozymes act in a target-specific manner and therefore may act as a toxic agent to a pathogen (such as bacteria) or a selected cell (such as a diseased cell). In accordance with the present invention, the multi-ribozymes may comprise a) a trans-acting ribozyme or toxic agent flanked by 5' and 3' autocatalytically cleaving ribozymes or enhanced autocatalytically cleaving ribozymes; b) a trans-acting ribozyme or toxic agent flanked by either a 5' or 3' autocatalytically cleaving ribozyme; or c) multi-transacting ribozymes and/or multiple toxic agents, flanked by one or both 5' and 3' autocatalytically cleaving ribozymes or enhanced autocatalytically cleaving ribozymes. Thus, the multi-ribozymes of the invention may be used to deliver one or more toxic agents to a bacteria or bacteria-infected cell or tissue. In accordance with the present invention the multi-transacting ribozymes may be targeted to the same site on the same RNA, different sites on the same RNA or different RNAs. In accordance with the present invention the multiple toxic agents may be targeted to the same site on the same target (such as a cellular RNA or protein), different sites on the same target or different targets.

The invention also provides for toxic agents or ribozymes containing modifications which enhance stability and protect against degradation. Examples of such modifications include those which protect against degradation by endonucleases such as modifications to the structure of the nucleotides and stabilizing hairpin loops in or near the ribozyme cassette. In one embodiment, the present invention a toxic agent or ribozyme is stabilized by a 3' hairpin loop.

The present invention further provides for regulating the cellular distribution of the trans-acting ribozymes and toxic agents when delivered to a eukaryotic cell. The present invention encompasses the use of combinations of slow cleavage and enhanced cleavage autocatalytically cleaving ribozymes to regulate the nuclear and cytoplasmic accumulation and distribution of the trans-acting ribozymes or toxic agents.

The invention additionally provides nucleic acids and expression cassettes which encode the toxic agent and/or ribozymes of the invention. These nucleic acids can be used to express the toxic agent and/or ribozyme of the invention at the selected site. In one embodiment, the nucleic acid comprise a tissue-specific promoter operably linked to a toxic agent. In another embodiment, the nucleic acids and expression cassettes of the invention comprise a tissue-specific promoter operably linked to a sequence encoding a catalytic ribozyme comprising one or more target RNA-specific trans-acting ribozymes and one or more toxic agents. In another embodiment, the nucleic acids comprise a pathogen-specific promoter from a sequence encoding a toxic agent. In another embodiment, the nucleic acids and expression cassettes of the invention comprise a pathogen-specific promoter operably linked to a sequence encoding a 5' autocatalytically cleaving ribozyme sequence, a catalytic ribozyme comprising one or more target RNA-specific trans-acting ribozymes and/or pathogen-specific toxic agents, and a 3' autocatalytically cleaving ribozyme sequence. In accordance with the present invention, the expression cassettes may be engineered to express two or more multi-ribozymes containing trans-acting ribozymes which act on the same or different targets. The expression cassettes may also be engineered to express two or more multi-ribozymes containing 5' and 3' autocatalytically cleaving ribozymes with either slow or enhanced cleavage activity.

In other embodiments, the invention provides nucleic acids and expression cassettes which encode multi-ribozymes with altered cleavage sites, so that the 5' and/or 3' autocatalytically cleaving ribozymes have enhanced activity, resulting in the more effective and efficient release of the targeted internal ribozymes or toxic agents. In an additional preferred embodiment the invention provides nucleic acids which encode multi-ribozymes with one or more trans-acting ribozymes, resulting in the more effective and efficient cleavage of target RNA. In an additional embodiment, the invention provides for nucleic acid that encode one or more ribozyme cassette each containing a) a 5' autocatalytically cleaving ribozyme sequence, b) catalytic ribozymes comprising one or more target RNA-specific trans-acting ribozymes and/or one or more toxic agents and c) a 3' autocatalytically cleaving ribozyme. In another embodiment, the expression cassettes encode autocatalytically cleaving ribozymes combinations of slow and enhanced cleavage activities resulting in a distribution of liberated trans-acting ribozymes or toxic agents between the nucleus and cytoplasm of a eukaryotic cell. In yet another embodiment, the expression cassette encodes enhanced autocatalytically cleaving ribozymes resulting in an increase accumulation of the liberated trans-acting ribozymes or toxic agent in the nucleus.

In another preferred embodiment the present invention relates to a toxic agent or a trans-acting ribozyme which targets any cellular, viral, bacterial, fungal, or other single or multicellular organism from any known taxonomic family, genus, or species, and from previously unknown, or uncharacterized organism. Another embodiment of the invention relates to a toxic agent which is lethal to a pathogen such as a bacteria, fungus, yeast, diseased cell. The present composition of matter has resulted from the development of a new process that delivers a series of ribozymes or toxic agents directed against fundamental and essential cellular processes specific to a targeted microorganism through an inactivated, altered, virus (virion), bacteriophage, or abiologic delivery vehicles, capable of delivering a nucleic acid containing the toxic agent(s) and/or ribozyme(s) into the targeted microorganism. The microorganisms may be any virus, nonvirus, bacterium, or lower eukaryotes such as fungi, yeast, parasites, protozoa, or other eukaryotes that may be consider normal flora or pathogens of humans, animals, fish, plants, or other forms of life. Thus, the invention has important implications in the eradication of drug-resistant pathogens.

In several embodiments of the invention, toxic agents or ribozymes of the invention are particularly suited as antimicrobial therapeutics. For example, upon nucleic acid hybridization with the target RNA transcript, a ribozyme-RNA complex achieves a catalytic form that acts as a nuclease to cleave the targeted RNAs. Thus, cleavage deprives the invading microorganism of essential cellular processes which then kills or renders it less fit.

A toxic agent of the invention may also be used as an antimicrobial therapeutic. A toxic agent may be used alone, or in combination with one or more other toxic agents. Thus, delivery of a toxic agent to an invading microorganism, kills or render it less fit.

A toxic agent may also be used in combination with one or more ribozymes. Further, a combination of ribozymes and toxic agents may be used as an antimicrobial therapeutic. These approaches offer advances for antimicrobial therapeutics: (1) the preparation bypasses any de novo built-in drug resistance, which sophisticated microbes will be expected to have or develop (2) cells are generally not capable of counteracting ribozymes delivered into them, (3) microbes have several broad RNA targets and non-RNA targets that can be attacked in simultaneously with probable synergy, (4) the custom design of the present delivery vehicle can be readily tailored to different families of organisms or different species of organisms, (5) the modified delivery vehicle is a construct easy to assemble and manufacture, (6) the preparation can be applied topically or it can be delivered via injection, inhalation, or ingestion, (7) the preparation can be lyophilized and thus confer stability to the antimicrobial therapeutic, (8) the inhalant, ingested or topical form of the antimicrobial therapeutic reduces the immunogenicity of the therapeutic preparations as opposed to its parenteral use, and (9) animal test systems exist that enable the evaluation of the ribozymes and/or toxic agents of the invention, in a measured, incremental fashion to quickly determine the efficacy of the antimicrobial therapeutic agent. Therefore, the unique delivery approach and an aggressive mechanism for depriving the microbial cells of essential or important gene products can achieve the timely defeat of microbes within the host.

The targets of the antimicrobial ribozyme therapeutics described herein are the RNAs of invading or normal flora microorganisms. The targets of the antimicrobial toxic agent therapeutics described herein include RNAs, proteins, genes and other molecules of invading or normal flora microorganisms. The invention provides the delivery of a series of ribozymes and/or toxic agents directed towards essential, housekeeping, or virulence genes of one or a series of candidate microorganisms. In one embodiment, a ribozyme is particularly suited as an active component of the present antimicrobial therapeutic in that it is a catalytic RNA molecule that cleaves RNA in a sequence specific manner. Therefore, in one embodiment, the catalytically active component of the therapeutic contains trans-acting ribozyme(s) that have been designed to inactivate RNA coding for components of the microbial cell. In another embodiment, ribozymes (such as 5' and 3' autocatalytic cis-acting ribozymes) of the invention are used to deliver a toxic agent (such as a nucleic acid) of the invention. For example, toxic agent(s) may be placed between the 5' and 3' autocatalytic cis-acting ribozymes, and thus the cis-acting ribozymes act to release the toxic agent(s). Inactivation of essential proteins and virulence determinants render the invading microbes inactive or slow their growth, while at the same time, the essential processes of the host are not affected.

At the molecular genetic level the coding sequence for a toxic agent, ribozyme, or multi-ribozyme of the invention may be placed under the control of one or more of the following genetic elements: a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of ribozyme and/or toxic agent expression. This genetic information may be delivered into the microbe by either a modified virus or abiologic delivery vehicle.

The present invention also relates to the delivery of the toxic agents of the invention to cell or pathogen by abiologic or biologic systems. In a specific embodiment, a toxic agent of the invention is delivered to a bacterial cell by a bacteriophage capable of infecting a pathogenic bacteria. In a further embodiment, bacteriophage are selected for their ability to infect a particular species of bacteria, and are used to deliver a toxic agent for the eradication of such bacterial species from a host.

In one embodiment of the present invention the nucleic acids encoding a toxic agent and/or ribozyme are unique in that they contain sufficient genetic information for expression of the toxic agent(s) and/or ribozyme(s) and such genetic information necessary and sufficient for its assembly and delivery to the targeted microorganism, but does not include nucleic acids native to the virus. Thus, the virion can serve as a molecular vehicle that delivers the inactivating ribozyme(s) and/or toxic agent(s). Alternatively, an abiologic delivery system (e.g., liposomes) can be used to package nucleic acid carrying the genetic elements necessary and sufficient for the proper expression of the ribozyme(s) and/or toxic agent(s).

The present invention further encompasses the use of a toxic agent and/or ribozymes of the present invention for the treatment of disease, viral infection, parasitic infection and microbial infection. The present invention further relates to a method of treating a subject having a proliferative disease of a specific tissue by inhibiting cell proliferation in the tissue, comprising administering to the subject a toxic agent and/or ribozyme operably linked to a tissue-specific promoter sequence, which promoter is specific for the diseased tissue, and whereby the ribozme and/or toxic agent encoded by the nucleic acid is expressed, cell proliferation is inhibited, and the proliferative disease is treated. The present invention further relates to a method of treating a subject having a pathogenic infection or disease by inhibiting replication of the pathogen, comprising administering to the subject a toxic agent and/or ribozyme operably linked to a pathogen-specific promoter sequence, whereby the ribozyme and/or toxic agent encoded by the nucleic acid is expressed, the pathogen is inhibited from replicating or is killed or rendered less fit, and the infection or disease is treated. The present invention encompasses the toxic agent (s) and/or ribozyme(s) of the present invention in pharmaceutical formulations.

The present invention further encompasses the use of the toxic agents and/or ribozymes of the present invention for research and screening purposes. In one embodiment of the present invention, the ribozymes and/or toxic agents may be used to screen for viral, microbial, prokaryotic, or eukaryotic gene products or molecules to be targeted in order to effectively inhibit the selected virus or microbial agent or selected cell.

In yet another embodiment, the present invention relates to a novel vector encoding the toxic agent(s) and/or ribozyme(s). The novel vectors of the present invention encode one or more toxic agents and/or ribozyme(s) which are rapidly and effectively expressed in a cell or pathogen. The novel vectors of the present invention may encode unique 5' and 3' autocatalytically cleaving activity, so that the one or more internally encoded ribozymes and/or toxic agents are rapidly and effectively released. The novel vectors of the present invention may be used to engineer a wide variety of toxic agents and/or ribozymes including, but not limited to, tissue-specific, pathogen-specific, promoter-specific, antimicrobial specific, antiviral specific, anticancer specific, antitumor specific, or target-specific.

4. BRIEF DESCRIPTION OF THE FIGURES

FIG. 1A The sequence of the LEASHI promoter (SEQ ID NO:1).

FIG. 1B The sequence of a modified rrnB promoter (SEQ ID NO:2).

FIG. 2 Sequence of the DicF1 molecule (SEQ ID NO:3).

FIG. 3 Diagram and nucleotide sequence of the pClip ribozyme cassette (SEQ ID NOS:4–5).

FIG. 4 Diagram and nucleotide sequence of the pChop ribozyme cassette (SEQ ID NOS:6–7).

FIG. 5 Schematic diagram of the pSnip ribozyme cassette. pSnip includes sequences of the pClip triple ribozyme cassette, catalytic core targeted ribozymes comprising two linked trans-acting ribozymes, and sequences from the pChop triple ribozyme cassette.

Figure 6A:
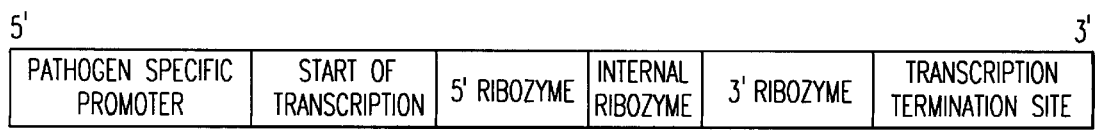
FIG. 6A shows a schematic of DNA encoding the ribozyme used in the molecular sequence of events in ribozyme maturation and action.
Figure 6B:
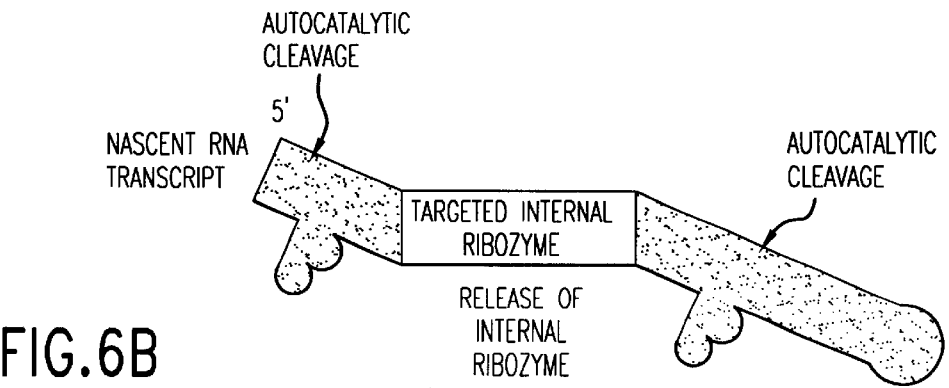
FIG. 6B shows the primary RNA transcript. Autocatalytic cleavage takes place upon completion of transcription.
Figure 6C:
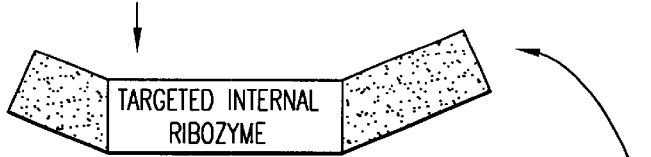
FIG. 6C shows the release of the trans-acting ribozyme. As a direct result of cleavage of the two cis-acting ribozymes, the internal ribozyme containing a reverse and complementary sequence to the mRNA target is released.
Figure 6D:
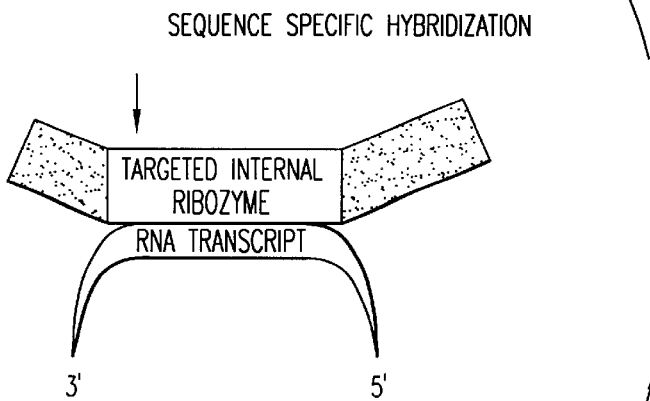

FIG. 6D shows the sequence specific hybridization of the ribozyme. The internal or trans-acting ribozymes comprise two trans-acting ribozymes linked by a short nucleotide "spacer". Each of the two trans-acting ribozymes contain a sequence that is reverse complementary to the targeted message of the same or at different sites. The ribozyme is synthesized at a concentration sufficient to locate and hybridize to all or substantially all targeted transcripts.

Figure 6E:
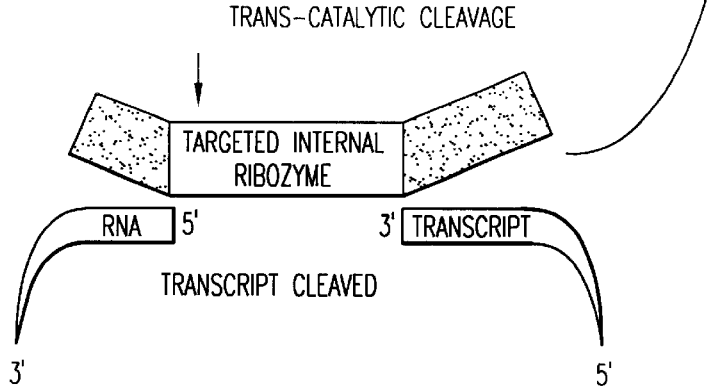

FIG. 6E shows the trans-catalytic cleavage. Upon hybridization of the internal trans-acting ribozyme to the targeted mRNA transcript, the internal ribozyme achieves a catalytic topology and cleaves the targeted message. Upon cleavage the trans-acting ribozyme is released and its activity and function are recycled.

5. DETAILED DESCRIPTION OF THE INVENTION

The present invention relates to toxic agent(s) and/or ribozyme(s) and their use in a tissue-specific, target-specific, or pathogen-specific manner for the treatment of disorders and disease related to bacterial, parasitic or viral infections or to cellular proliferation, and cancers. The ribozymes and/or toxic agents of the present invention may be engineered to target one or more specific RNAs contained in a specific cell or tissue in the host. The ribozymes of the present invention may also be engineered to target one or more specific RNAs encoded by a specific pathogen, virus, or microbial agent. The toxic agents of the present invention may also be engineered to target one or more specific RNAs or proteins or molecules of a specific pathogen, virus, or microbial agent.

The present invention also relates to toxic agents which are lethal to a selected pathogen. The toxic agents of the invention comprise toxic proteins which cause lethality to a pathogen or selected cell (e.g., a diseased cell) or which render the pathogen or selected cell less fit. In one embodiment, such toxic proteins of the invention are lethal when overexpressed in a pathogen or selected cell. In other embodiments, a toxic protein is an exogenous protein that is toxic when expressed in a pathogen or selected cell. A toxic protein of the invention may further be engineered to have increased toxicity. For example, many methods are known in the art for introducing mutations, deletion, insertions etc. into a known sequence. Thus, optimization of a toxic protein is provided. The invention also provides methods for inhibiting the toxicity of a toxic protein, so that the toxic protein may be produced or manufactured in a producing cell. Inhibiting the toxicity may be performed by any methods known in the art, for example, the toxic protein may be expressed from an inducible promoter which allows expression to be turned on/off under appropriate conditions. A toxic protein may be expressed in a cell without causing lethality in the cell by overexpressing an antidote protein in the same cell. Other methods will be apparent to one skilled in the art and are within the scope of the invention.

In another embodiment, the toxic agents of the invention comprise antisense molecules designed to have enhanced inhibition of target RNAs. The toxic agents which comprise antisense molecules of the invention are engineered to more specifically bind target RNAs in that the sequences of such toxic antisense molecules are designed to have increased complementarity to a target sequence such as an essential RNA of a pathogen or selected cell. Such toxic antisense molecules are therefore more specific to their targets and hence, have increased efficacy.

The invention provides antisense toxic agents and ribozymes which are also modified with a hairpin structure to create a more stable molecule. The antisense toxic agents of the invention may also be expressed to a high level in a target pathogen or cell by any method known or cell by any method known in the art. For example, an antisense toxic agent may be expressed in trans from a multi-copy expression plasmid using a strong regulatable promoter. The antisense toxic agent may also be operably linked to a tissue-specific or pathogen-specific promoter such that the antisense molecule is only expressed in a pathogen or cell which uses the same promoter.

In another embodiment of the invention the toxic agents comprise sense RNA molecules targeted to antisense RNAs which are required for the survival of the pathogen or cell. For example, an antidote of a toxic protein (such as an addiction system toxin) may be in the form of an antisense molecule which regulates the expression of the toxin. Such an antisense antidote allows the pathogen or cell to survive in the presence of such toxin. The invention provides inhibition of the antisense antidote by a toxic agent in the form of a sense RNA molecule.

The present invention relates to promoter elements which are pathogen-specific. The invention relates to promoter elements which are used to achieve pathogen-specific expression of the toxic agent(s) and/or ribozyme(s) of the present invention. The present invention relates to promoter elements which are tissue-specific. The invention relates to promoter elements which are used to achieve tissue-specific expression of the toxic agent(s) and/or ribozyme(s) of the present invention. The invention also relates to a vector or plasmid origin of replication which modulates specificity of the replication of a vector or plamid in a cell or pathogen. The invention also relates to the copy number of a vector or plasmid in a selected cell or pathogen to modulate the dose of the toxic agent and/or ribozyme.

In accordance with the present invention, the toxic agents may be designed to encode two or more toxic proteins, toxic antisense, or toxic sense molecules. When more than one toxic agent is encoded in a nucleic acid delivered to a pathogen or selected cell, such toxic agents may be directed to the same target, or different targets of the pathogen or selected cell. Thus, for example, a combination of two or more toxic antisense molecules may be delivered to a pathogen (such as E. coli, P. aeruginosa, etc.) in order to cause lethality. In this embodiment, the toxic antisense may be directed to the same RNA target, or different RNA targets. When different targets of a pathogen or cell are targeted, such targets may be involved in the same biological pathway within the pathogen or different biological pathways.

In yet another embodiment of the inventions, a toxic agent comprises a trans-acting catalytic ribozyme. In a preferred embodiment of the invention, the trans-acting ribozyme is part of a multi-ribozyme or ribozyme cassette, as derived below.

Catalytic multi-ribozyme(s) contain two separable functional regions including a "catalytic core" which cleaves the target RNA or RNAs which include a target RNA-specific binding site, and flanking regions which include the cis-acting ribozyme. The catalytic core contains one or more ribozymes known as trans-acting ribozymes. In some embodiments of the invention, the catalytic core contains one or more toxic agents of the invention. The flanking regions are located nearby or adjacent to the catalytic core, and contain ribozymes known as autocatalytically cleaving ribozyme sequences. A catalytic core in combination with one or more flanking region(s) as used herein is referred to as a ribozyme "cassette". By nucleic acid complementarity, the binding site directs the trans-acting ribozyme core to cleave a specific site on the target RNA molecule.

In particular, the multi-ribozymes of the present invention are designed to have improved properties to enhance their efficacy in cleaving a target RNA. The multi-ribozymes of the present invention comprise a trans-acting ribozyme and 5' and 3' flanking autocatalytically cleaving ribozymes or may comprise only the 5' or the 3' flanking autocatalytically cleaving ribozyme. The flanking autocatalytically cleaving ribozymes are cis-acting and act to liberate the trans-acting ribozyme or toxic agent. The autocatalytically cleaving ribozymes of the present invention may have slow cleavage activity or enhanced cleavage activity. The combination of slow cleaving autocatalytic ribozymes followed by enhanced cleaving autocatalytic ribozymes results in the distribution of trans-acting ribozymes between the nucleus and the cytoplasm of a eukaryotic cell. The use of enhanced cleaving autocatalytic ribozymes results in primarily a nuclear accumulation of the trans-acting ribozymes and the use of slow cleaving ribozymes results in primarily a cytoplasmic accumulation of the trans-acting ribozymes.

In accordance with the present invention, the multi-ribozymes may be designed to release two or more linked trans-acting ribozymes, or one or more toxic agents, or a combination thereof. The trans-acting ribozymes and/or toxic agents may be targeted to the same site on the same target, different sites on the same target or different targets.

Use of a "spacer" for linking the ribozymes or toxic agents together is provided by the invention. In one specific embodiment, but not by way of limitation, the ribozymes and/or ribozyme cassettes are linked together by a short "spacer" of 4–5 nucleotides.

The invention also provides for the multi-ribozymes contain a stabilizing hairpin loop. In a preferred embodiment, the trans-acting ribozymes are stabilized by a nucleotide hairpin loop. In one embodiment, the one or more trans-acting ribozymes are stabilized by a hairpin loop that is 3' to the trans-acting ribozymes.

The present invention relates to nucleic acids encoding the tissue-specific or pathogen-specific ribozymes of the present invention. The nucleic acids of the present invention may comprise a tissue-specific or pathogen-specific promoter operably linked to a sequence encoding a) a 5' autocatalytically cleaving ribozyme, b) an internal targeted catalytic ribozyme containing one or more target RNA-specific trans-acting ribozymes and/or one or more toxic agents, and c) a 3' autocatalytically cleaving ribozyme sequence. In a preferred embodiment, the invention provides nucleic acids which encode multi-ribozymes with altered cleavage sites, so that the 5' and/or 3' autocatalytically cleaving ribozymes have enhanced activity, resulting in the more effective and efficient release of the targeted internal ribozymes or toxic agents. In an additional preferred embodiment the invention provides nucleic acids which encode multi-ribozymes with one or more trans-acting ribozymes and/or toxic agent, resulting in the more effective and efficient targeting of RNA-target(s).

In another embodiment, the invention relates to nucleic acids which encode a toxic agent or ribozymes which are targeted by their delivery vehicle.

The present invention further relates to the use of a wide variety of vehicles to deliver the toxic agents or ribozymes to a target, including virions and viral vectors to package and deliver the DNA encoding the ribozymes and/or toxic agents; non-viral expression vectors and non-biologic vehicles, including liposomes and liposome-DNA and lipid-DNA complexes to deliver and target the DNA encoding the multi-ribozymes and/or toxic agents to the host.

In accordance with the invention, the host to which the ribozymes and/or toxic agents are delivered may be cells in culture, tissues in culture, plants, animal models, animals, mammals, or humans.

The present invention further relates to pharmaceutical compositions comprising the toxic agents or ribozymes of the present invention and their delivery vehicles. The toxic agents and/or ribozymes of the present invention may be engineered for the treatment of a wide variety of disorders and diseases related to expression of a particular gene or genes, cellular overproliferation, hereditary disorders, cancers, tumors, viral infections, bacterial infection, fungal infection, parasitic infection, or other diseases.

In another embodiment of the present invention, the toxic agents and/or ribozymes of the present invention may also be used for in vitro screening purposes, e.g., to identify a gene product involved in cellular overproliferation or to identify a gene product critical for the survival of a virus or microbe.

In other embodiments the present invention relates to a toxic agent or a trans-acting ribozyme which targets any cellular, viral, bacterial, fungal, or other single or multicellular organism from any known taxonomic family, genus, or species, and from previously unknown, or uncharacterized organism. Another embodiment of the invention relates to a toxic agent which is lethal to a pathogen such as a bacteria, fungus, yeast, diseased cell. The present composition of matter has resulted from the development of a new process that delivers a series of ribozymes or toxic agents directed against fundamental and essential cellular processes specific to a targeted microorganism through an inactivated, altered, virus (virion), bacteriophage, or abiologic delivery vehicles, capable of delivering a nucleic acid containing the toxic agent(s) and/or ribozyme(s) into the targeted microorganism. The microorganisms may be any virus, nonvirus, bacterium, or lower eukaryotes such as fungi, yeast, parasites, protozoa, or other eukaryotes that may be consider normal flora or pathogens of humans, animals, fish, plants, or other forms of life. Thus, the invention has important implications in the eradication of drug-resistant pathogens.

5.1. Pathogen-Specific Toxic Agents

The invention provides specific nucleic acids which act as toxic agents and are therefore useful as antimicrobial agents. A variety of toxic agents are within the scope of the invention. For clarity, the toxic agents of the invention are described herein below in several sub-types. The toxic agents of the invention include but are not limited to antisense nucleic acids, toxic gene products, sense nucleic acids, and ribozymes.

5.1.1. Antisense Nucleic Acids

The invention provides specific nucleic acids which act as toxic agents and are therefore useful as antimicrobial agents. The invention relates to antisense RNA molecules which target an RNA of a pathogen or selected cell. Target RNAs of the invention may be pathogen-specific RNAs, tissue-specific cellular RNAs, or disease-specific RNAs. The invention also relates to modified and enhanced antisense nucleic acids which target pathogen-specific RNAs, tissue-specific cellular RNAs, or disease-specific RNAs.

The proposed target of the toxic antisense molecule of the invention is the RNA of a gene which plays a critical role in the survival of the pathogen, or which is essential to the pathogen's life cycle. The present invention also encompasses modifications to naturally occurring antisense molecules which modulate the expression of an essential gene product of a pathogen. For example, as described below, one proposed target of an antisense of the invention is the ftsZ gene whose gene product plays a critical role in the initiation of cell division of E. coli.

In a specific embodiment, the antisense sequence is based on DicF (Bouche F, et al., 1989, Mol Microbiol. 3:991–4). Such modified DicF sequence is referred to as DicF1 and is depicted in FIG. 2 (SEQ ID NO:3). Naturally occurring DicF is part of an intercistronic region that when expressed in Escherichia coli causes inhibition of cell division. This inhibition does not require the translation of DicF mRNA into protein, instead, DicF RNA exerts its inhibitory effect as an antisense molecule.

The proposed target of DicF is the ftsZ gene whose gene product plays a critical role in the initiation of cell division of E. coli. Temperature sensitive mutations of the ftsZ gene indicate that it is essential for viability of E. coli. DicF RNA is believed to bind specifically to the 5' untranslated region of ftsZ mRNA, thereby inhibiting ftsZ protein expression. Cells lacking the ftsZ protein are unable to divide and ultimately die. DicF homologs have been identified in a variety of other bacteria although it is not known whether they exert a similar function.

The present invention provides for modified DicF nucleic acids, called DicF1 or DicF1-like RNAs, which are used as antimicrobial agents, or toxic agents of the invention. DicF1 RNA is a superior antisense molecule as compared to the endogenous DicF RNA. It has been modified by increasing its complementarity to the ftsZ 5' untranslated mRNA. It is therefore more specific to its target and hence, has increased efficacy. An auto hairpin structure has further been enhanced to create a more stable molecule. The invention also relates to modifications of other naturally occurring antisense molecules, such as nucleotide sequences which have similar functions as DicF in modulating the expression of gene products essential to the pathogen's life cycle or survival. Such nucleic acid is referred to as a DicF1-like nucleic acid. In contrast to the endogenous DicF, the DicF1 or a DicF1-like nucleic acid of the invention may be expressed in trans from a multi-copy expression plasmid. Further, the DicF1 or DicF1-like nucleic acids may be operably linked to a variety of promoters that may be used to control the strength, timing, or tissue distribution of such expression. DicF1 or a DicF1-like nucleic acid may also be expressed in trans from a ribozyme cassette. The combination of these features results in DicF1 or DicF1-like nucleic acid being an effective antimicrobial agent against a pathogen (such as E. coli). In other embodiments, modifications to the sequence of an antisense of the invention allows targeting against a variety of other bacteria. In other embodiments, modifications to the sequence of an antisense of the invention allows targeting in a pathogen-specific manner. The invention also provides DicF1-like nucleic acids which may be used as toxic agents in bacteria, bacteria-infected cells, or other pathogens which have complementary RNA targets.

5.1.2. Toxic Gene Products

The present invention relates to the use of toxic gene products or toxic proteins as toxic agents for the treatment of disorders and disease related to bacterial, parasitic, fungal, or viral infections or to cellular proliferation, and cancers, or to diseased cells. A toxic gene product of the invention is any gene product (such as RNA or protein), which is toxic to a pathogen or selected cell (such as a diseased cell) Such toxic gene products may be naturally occurring (endogenous), or may be non-naturally occurring (exogenous) in the target pathogen or selected cell. A toxic agent of the invention may be a chromosomally encoded, plasmid encoded, pathogen encoded, synthetic, or encoded in any other nucleic acid or nucleotide sequence. The present invention provides toxic agents which are endogenous toxic gene products that are expressed in a pathogen or selected cell which kill or render the pathogen or selected cell less fit. The present invention also provides toxic agents which are exogenous toxic gene products that are introduced into or expressed in a pathogen or selected cell which kill or render the pathogen or selected cell less fit. A pathogen or selected cell which is less fit is one which is weakened, or which is more susceptible to chemical treatment (such as drugs, toxins, pharmaceuticals, mutagens, solvents, etc), or which is more susceptible to physical stress (such as temperature), or which is more susceptible to genetic alterations (such as by radiation or UV), or is more susceptible to environmental changes (such as available nutrients).

In several embodiments, the present invention provides the use of a plasmid addiction system protein as a toxic agent when expressed in bacteria or a selected cell. For example, in certain types of bacteriophage, the lysogenic (dormant) pathway is manifested by a bacterial cell maintaining only a single copy of the bacteriophage DNA in the form of a plasmid. In order to assure that both daughter bacterial cells receive a copy of the plasmid, a "plasmid addiction system" or "post-segregation system" is used by the cells which ensures that only bacterial cells which receive a copy of the plasmid will survive.

In one embodiment of the invention, a post-segregation system or plasmid addiction system toxin, is used as a toxic agent to a pathogen (such as bacteria) by overexpression of the toxin. Such overexpression of the toxin uncouples the toxin and the antidote, leading to toxicity, and preferably lethality, in the cell containing the overexpressed toxic agent. In another embodiment of the invention, a chromosomally encoded toxic gene product is used as a toxic agent to a pathogen by overexpression of the toxic gene product.

In another embodiment, the antidote of a toxin is the target of a trans-acting ribozyme or toxic agent of the invention. Thus, when the antidote is inactivated by the trans-acting ribozyme or toxic agent, the toxin is no longer neutralized or inactivated by the antidote, thus leading to toxicity, and preferably lethality.

In yet another embodiment, when the antidote is itself an antisense RNA, a sense RNA may be synthesized as a toxic agent and delivered to inactivate the antisense antidote. Thus, when the antidote is inactivated by the sense RNA, the antidote is no longer available to inactivate the toxin, thus leading to toxicity, and preferably lethality.

One example of an addiction system toxin that may be used in connection with the invention is Doc (death on curing; Lehnherr H, et al., 1993, J. Mol. Biol. 233:414–28). Doc acts as the cell toxin to which Phd (prevention of host death) is the antidote. In several embodiments of the invention, the toxic gene is placed under the control of an inducible promoter and is uncoupled from the antidote. In one embodiment, the promoter is the P1 lytic promoter P53. In a preferred embodiment, the promoter is the LEASHI promoter. In another specific embodiment of the invention, a consensus ribosome binding site (GGAGGTGXXXXATG, wherein X is any nucleotide) is inserted immediately upstream of the gene encoding the toxic agent (such as an addiction system toxin) and leads to increased expression of the toxic agent. The invention relates to the use of a combination of a promoters and a ribosome entry site(s) to modulate expression of a toxic agent or ribozyme. Examples of addiction system toxins or chromosomally encoded toxins which may be used in connection with the invention include but are not limited to ccdB, kid, perK, parE, doc, higB, chpAK, chpBK, kicB, hoc, srnB', flmA, pmdA, relF, gef, kilA, kilB, kilC, kilE, traL, traE, and kikA. Examples of antidotes which may be used as in the methods of the invention include but are not limited to ccdA, kis, pemI, parD, phd, higA, chpAI, chpBI, kicA, soc, srnC, flmB, pndB, sof, korA, korB, korC, korD, korE, and korF. Thus, the invention herein provides a method of using a an addiction system toxin (such as Doc) or other toxic protein, as a toxic agent of the invention. The invention also provides methods for inhibiting or inactivating antidotes of a toxin.

5.1.3. Ribozymes as Toxic Agents

The present invention provides methods by which a trans-acting ribozyme may be used as a toxic agent of the invention. Further, a multi-ribozyme may be used as an expression system for one or more toxic agents or trans-acting ribozymes. These ribozymes of the invention can be used, for example, to destroy tissue-specific disease, or to treat bacterial, viral, or parasitic infections. The ribozymes of the present invention may comprise one or more multi-ribozymes.

In accordance with the present invention, the multi-ribozyme may consist of one or more ribozymes or one or more ribozyme cassettes. Each cassette in turn may consist of a catalytic core (e.g., containing one or more trans-acting ribozymes or containing one or more toxic agents) and one or more flanking sequences. The catalytic core can act as a toxic agent in a pathogen, by specifically inhibiting a pathogen-specific target or tissue-specific target. Further, as described in sections below, the multi-ribozymes of the invention also provide a means of delivering toxic agents to a cell, and expressing toxic agents of the invention (including antisense RNA, toxic gene products, and/or trans-acting ribozymes) in a cell or tissue-specific, or pathogen-specific manner. In one embodiment, the ribozyme cassette may consist of a 5' autocatalytically cleaving ribozyme sequence, a core catalytic ribozyme comprising a trans-acting ribozyme and a 3' autocatalytically cleaving ribozyme. In another embodiment, the multi-ribozymes comprise a cassette including, the enhanced 5' and 3' auto-catalytically cleaving ribozyme sequence. In another embodiment, the multi-ribozymes contain one or more internal trans-acting ribozymes. Such trans-acting ribozymes can serve as toxic agents of the invention and may be directed to the same site on the same RNA, different sites on the same RNA, or different RNAs. Thus, trans-acting ribozymes of the invention are toxic agents which target a pathogen-specific RNA or tissue-specific RNA.

The ribozymes of the present invention possesses sufficient catalytic activity to inactivate the RNA of the targeted RNAs. From an antimicrobial perspective, hammerhead-type ribozymes are especially attractive since the molecule inactivates gene expression catalytically through the cleavage of the phosphodiester bond of the mRNA. Furthermore, hammerhead-type ribozymes have been re-engineered to function in an intermolecular or transducer (trans) acting state (Haseloffet al., 1988, Nature 334(6183):585–91; Uhlenbeck. O. C., 1987, Nature 328(6131):59). The catalytic activity of the ribozyme requires a sufficient concentration of the divalent cation, $Mg^{+2}$, and substrate. The substrate can have any sequence as long as the cleavages site contains the recognition element NUX, where N represents any nucleotide, U corresponds to uracil, and X is any nucleotide except G (Koizumi et al., 1989, Nucleic Acids Resonant. 17(17):7059–71). Ribozymes have been widely demonstrated to function in vivo (Christoffersen et al., 1995, J. Med. Chem. 38(12):2023–37; Inokuchi et al., 1994, J. Biol. Chem. 269(15):11361–6). The present invention improves the initial design of hammerhead-type ribozymes (Taira et al., 1991, NAR 19(9):5125–5130) by constructing multi-ribozymes consisting of ribozyme cassettes. Ribozyme cassettes contain one or more cis-acting hammerhead ribozymes flanking a ribozyme that inactivates the targeted RNA(s) as well as one or more flanking sequences. Upon transcription the targeted ribozyme is released as a 60–70 base transcript which not only improves its specificity by reducing non-specific interactions but also improves its catalytic activity as well. This invention includes modifications to and use of the ribozyme described in U.S. Ser. No. 08/554,369 and PCT publication No.WO98/24925, which are incorporated by reference herein in their entirety.

5.2. Nucleic Acids Encoding Toxic Agents or Ribozymes

The invention also provides nucleic acids which encode the ribozymes and/or toxic agents of the invention. These nucleic acids can be used to express the ribozymes or toxic agents of the invention at the selected site. The site can be tissue-specific in the case of treating tissue-specific cancers or disease, or it can be pathogen-specific in the case of ribozymes or toxic agents that prevent replication of infectious agents to treat infection (e.g., hepatitis, herpes, malaria, tuberculosis, bacterial infections etc.). The invention provides nucleic acids which encode toxic agent(s) and/or ribozyme(s) which are target-specific. The invention also provides nucleic acids which encode toxic agent(s) and/or ribozyme(s) operably linked to a tissue-specific or pathogen-specific promoter.

There are several options for constructing the multi-ribozyme encoding sequences: 1) ribozymes directed to different targets in the same pathogen 2) multiple copies of the same ribozyme 3) multiple ribozymes directed to multiple targets, and 4) multiple ribozymes directed to different sites on the same target. There are also several options for constructing the toxic agent encoding sequences: 1) toxic agents directed to different targets in the same pathogen 2) multiple copies of the same toxic agent 3) multiple toxic agents directed to multiple target, and multiple toxic agents directed to different sites on the same target. Further, toxic agents and ribozymes may be combined in various ways, e.g., a multi-ribozyme and a nucleic acid encoding a toxic agent may be engineered in a single construct under one promoter. The promoter can have the chosen level of specificity as described herein.

The nucleic acids of the invention encode one or more toxic agents of the invention. As described herein, such toxic agents include toxic proteins, toxic antisense molecules, toxic sense molecules, and ribozymes. Thus, nucleic acids encoding toxic proteins of the invention include but are not limited to addiction system toxins. The invention further relates to modified and enhanced addiction system toxins which have been engineered to be more toxic or more specific to a particular target pathogen. The present invention relates to nucleic acids encoding antisense molecules targeted to RNA of a gene which plays a critical role in the survival of the pathogen, or which is essential to the pathogen's life cycle. The present invention also encompasses nucleic acids comprising modifications to naturally occurring antisense molecules which modulate the expression of an essential gene product of a pathogen.

The nucleic acids of the invention also relates to those encoding antisense molecules of the invention. The invention provides modified and enhanced antisense molecules which have enhanced stability, enhanced complementarity to a target RNA, or enhanced specificity for a target RNA or target pathogen. The invention also relates to nucleic acids encoding modified naturally occurring antisense molecules, such as nucleotide sequences which have similar functions as DicF in modulating the expression of gene products essential to the pathogen's life cycle or survival.

The nucleic acids of the invention also relate to nucleic acids encoding sense RNA molecules capable of targeting an essential antisense molecule.

The nucleic acid, encoding a toxic agent selected from the group consisting of ccdB, kid, perK, parE, doc, higB, chpAK, chpBK, kicB, hoc, srnB', flmA, pmdA, relF, gef, kilA, kilB, kilC, kilE, traL, traE, and kikA is provided. The nucleic acid encoding the toxic agent DicF1, or DicF1-like, is provided.

In several embodiments, nucleic acids of the invention encode a catalytic multi-ribozyme(s) that contains two separable functional regions including a) a highly conserved catalytic sequence (also known as the "catalytic core") which cleaves the target RNA, and b) flanking regions which include cis-acting autocatalytically cleaving ribozyme(s). As described above, the catalytic core consists of one or more trans-acting ribozyme(s) and/or one or more toxic agent(s). The present invention provides nucleic acid which encode an internal targeted ribozyme containing two or more trans-acting ribozymes, wherein each of the separate trans-acting ribozymes can be targeted to the same or different target RNA molecules. By nucleic acid complementarity, the binding site directs the ribozyme core to cleave a specific site on the target RNA molecule. The length of flanking sequences have implications not only for specificity, but also for the cleavage efficiency of the individual ribozyme molecules. In the present catalytic ribozyme, the flanking sequences are highly specific for the target RNA, yet allow ready dissociation from the target RNA once cleavage occurs. This permits cycling of the ribozyme and reduces the amount of ribozyme required to be effective. A range of binding/dissociation values from 16–21 Kcal is expected to be effective. The present invention provides nucleic acid which encode a two or more toxic agents, wherein each of the toxic agents can be targeted to the same or different target molecules.

The invention additionally provides nucleic acids and expression cassettes which encode the toxic agent and/or ribozymes of the invention. These nucleic acids can be used to express the toxic agent and/or ribozyme of the invention at the selected site. In one embodiment, the nucleic acid comprise a tissue-specific promoter operably linked to a toxic agent. In another embodiment, the nucleic acids and expression cassettes of the invention comprise a tissue-specific promoter operably linked to a sequence encoding a catalytic ribozyme comprising one or more target RNA-specific trans-acting ribozymes and one or more toxic agents. In another embodiment, the nucleic acids comprise a pathogen-specific promoter from a sequence encoding a toxic agent. In another embodiment, the nucleic acids and expression cassettes of the invention comprise a pathogen-specific promoter operably linked to a sequence encoding a 5' autocatalytically cleaving ribozyme sequence, a catalytic ribozyme comprising one or more target RNA-specific trans-acting ribozymes and/or pathogen-specific toxic agents, and a 3' autocatalytically cleaving ribozyme sequence. In accordance with the present invention, the expression cassettes may be engineered to express two or more multi-ribozymes containing trans-acting ribozymes which act on the same or different targets. The expression cassettes may also be engineered to express two or more multi-ribozymes containing 5' and 3' autocatalytically cleaving ribozymes with either slow or enhanced cleavage activity.

In other embodiments, the invention provides nucleic acids and expression cassettes which encode multi-ribozymes with altered cleavage sites, so that the 5' and/or 3' autocatalytically cleaving ribozymes have enhanced activity, resulting in the more effective and efficient release of the targeted internal ribozymes or toxic agents. In an additional preferred embodiment the invention provides nucleic acids which encode multi-ribozymes with one or more trans-acting ribozymes, resulting in the more effective and efficient cleavage of target RNA. In an additional embodiment, the invention provides for nucleic acid that encode one or more ribozyme cassette each containing a) a 5' autocatalytically cleaving ribozyme sequence, b) catalytic ribozymes comprising one or more target RNA-specific trans-acting ribozymes and/or one or more toxic agents and c) a 3' autocatalytically cleaving ribozyme. In another embodiment, the expression cassettes encode autocatalytically cleaving ribozymes combinations of slow and enhanced cleavage activities resulting in a distribution of liberated trans-acting ribozymes or toxic agents between the nucleus and cytoplasm of a eukaryotic cell. In yet another embodiment, the expression cassette encodes enhanced autocatalytically cleaving ribozymes resulting in an increase accumulation of the liberated trans-acting ribozymes or toxic agent in the nucleus.

The complexity of human RNA is about 100 fold lower than that for human DNA, and specificity can be achieved with as few as 12–15 base pairs. The stability of the RNA—RNA duplex is effected by several factors, such as GC content, temperature, pH, ionic concentration, and structure. The nearest neighbor rules can provide a useful estimate of the stability of the duplex (Castanotto et al. "Antisense Catalytic RNAs as Therapeutic Agents" *Advances in Pharmacol.* 25:289–317, 1994).

The catalytic ribozyme of the invention also includes a catalytic sequence, which cleaves the target RNA near the middle of the site to which the target RNA-specific sequences bind. In the hammerhead-type of ribozyme, the catalytic sequence is generally highly conserved. The conserved catalytic core residues are 5' CUGANGA 3' and 5' GAAA 3' linked by an evolutionarily conserved stem-loop structure.

The most conserved and probably most efficiently cleaved sequence on the target RNA is 5' GUC 3'. However, NUX (wherein X=A, U or C) can also be cleaved efficiently. Such cleavage sites are ubiquitous in most RNAs allowing essentially all RNA's to be targeted (Whitton, J. Lindsay "Antisence Treatment of Viral Infection" *Adv. in Virus Res.* Vol. 44, 1994).

With regard to the selection of the appropriate sites on target RNA, it is known that target site secondary structure can have an effect on cleavage in vitro (Whitton, 1994 supra). A number of procedures are available to select accessible sites in RNA targets. In a preferred procedure, a library screen may be employed to select appropriate sites on the target RNA. Accessibility of the selected site may then be confirmed using techniques known to those skilled in the art. Thus, the selected target molecule's sequence can be routinely screened for potential secondary structure, using the program RNAFOLD (from the PCGENE group of programs or available on the Internet). Thus, reasonable predictions of target accessibility can be made. Computer assisted RNA folding (Castanotto et al., 1994), along with computational analysis for 3-dimensional modeling of RNA (Major et al., *Science* 253:1255–1260, 1991 and Castanotto et al., 1994) is certainly effective in guiding the choice of cleavage sites.

The nucleic acid, wherein at least one trans-acting ribozyme is targeted to a ccdA, kis, pemI, parD, phd, higA, chpAI, chpBI, kicA, soc, sos, srnC, flmB, pndB, sof, korA, korB, korC, korD, korE, or korF transcript of the pathogen is provided. The nucleic acid, wherein at least one trans-acting ribozyme is targeted to the rpoA transcript of the pathogen is provided. The nucleic acid, wherein at least one trans-acting ribozyme is targeted to the secA transcript of the pathogen is provided. The nucleic acid, wherein at least one trans-acting ribozyme is directed to the dnaG transcript of the pathogen is provided. The nucleic acid, wherein at least one trans-acting ribozyme is directed to the ftsZ transcript of the pathogen is provided A nucleic acid encoding a multi-ribozyme can encode all or some of the above trans-acting ribozymes. The ribozymes can all be under the control of a single promoter.

At the molecular genetic level the coding sequence for a toxic agent, ribozyme, or multi-ribozyme of the invention may be placed under the control of one or more of the following genetic elements: a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of ribozyme and/or toxic agent expression. This genetic information may be delivered into the microbe by a either a modified virus or abiologic delivery vehicle.

The present invention also relates to the delivery of the toxic agents of the invention to cell or pathogen by abiologic or biologic systems. In a specific embodiment, a toxic agent of the invention is delivered to a bacterial cell by a bacteriophage capable of infecting a pathogenic bacteria. In a further embodiment, bacteriophage are selected for their ability to infect a particular species of bacteria, and are used to deliver a toxic agent for the eradication of such bacterial species from a host.

In one embodiment of the present invention the nucleic acids encoding a toxic agent and/or ribozyme are unique in that they contains sufficient genetic information for expression of the toxic agent(s) and/or ribozyme(s) and such genetic information necessary and sufficient for its assembly and delivery to the targeted microorganism, but does not include nucleic acids native to the virus. Thus, the virion can serve as a molecular vehicle that delivers the inactivating ribozyme(s) and/or toxic agent(s). Alternatively, an abiologic delivery system (e.g., liposomes) can be used to package nucleic acid carrying the genetic elements necessary and sufficient for the proper expression of the ribozyme(s) and/or toxic agent(s).

In yet another embodiment, the present invention relates to a novel vector encoding the toxic agent(s) and/or ribozyme(s). The novel vectors of the present invention encode one or more toxic agents and/or ribozyme(s) are rapidly and effectively expressed in a cell or pathogen. The novel vectors of the present invention may encode unique 5' and 3' autocatalytically cleaving activity, so that the one or more internally encoded ribozymes and/or toxic agents are rapidly and effectively released. The novel vectors of the present invention may be used to engineer a wide variety of toxic agents and/or ribozymes including, but not limited to, tissue-specific, promoter-specific, pathogen-specific, antimicrobial specific, anti-viral specific, anticancer specific, anti-tumor specific, or target-specific.

The present invention relates to nucleic acids encoding promoter elements which are pathogen-specific. The invention relates to promoter elements which are used to achieve pathogen-specific expression of the toxic agent(s) and/or ribozyme(s) of the present invention. The present invention relates to promoter elements which are tissue-specific. The invention relates to promoter elements which are used to achieve tissue-specific expression of the toxic agent(s) and/or ribozyme(s) of the present invention. The invention also relates to a vector or plasmid origin of replication which modulates specificity of the replication of a vector or plamid in a cell or pathogen. The invention also relates to the copy number of a vector or plasmid in a selected cell or pathogen to modulate the dose of the toxic agent and/or ribozyme.

5.2.1. Eucaryotic and Procaryotic Expression Vectors

The present invention encompasses expression systems, both eucaryotic and procaryotic expression vectors, which may be used to express the toxic agents and/or multi-ribozymes of the invention. The DNA expression vectors and viral vectors containing the nucleic acids encoding the toxic agents (including antisense RNA, ribozymes, or toxic gene products) of the present invention may be produced by recombinant DNA technology using techniques well known in the art. Thus, methods for preparing the expression vectors and viral vectors of the invention by expressing nucleic acid encoding a toxic agent and/or multi-ribozyme sequences are described herein. Methods which are well known to those skilled in the art can be used to construct expression vectors containing gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, nucleic acids capable of encoding a toxic agent and/or ribozyme sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the selected toxic agent and/or multi-ribozyme of the invention. Such host-expression systems represent vehicles by which the sequences encoding the toxic agents or ribozymes of the invention may be introduced into cells, tissues, or pathogens both in vivo and in vitro but also represent cells which may, when transformed or transfected with the appropriate nucleotide coding sequences, to express a toxic agent and/or ribozymes of the invention. These include but are not limited to microorganisms such as bacteria transformed with recombinant bacteriophage DNA, plasmid DNA or cosmid DNA expression vectors containing selected toxic agent(s) and/or multi-ribozyme coding sequences; yeast (e.g., Saccharomyces, Pichia) transformed with recombinant yeast expression vectors containing the selected toxic agent(s) and/or multi-ribozyme coding sequences; insect cell systems infected with recombinant virus expression vectors (e.g., baculovirus) containing the selected toxic agent(s) and/or multi-ribozyme coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing selected toxic agent(s) and/or multi-ribozyme coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter, the vaccinia virus 7.5 K promoter).

5.3. Delivery and Expression of Toxic Agents

The invention also provides a novel vehicle for the delivery of toxic agents or ribozymes of the invention. The invention encompasses DNA expression vectors and viral vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences or RNAs in the host cell or pathogen. A key to the present invention is the strategy used to deliver the toxic agent and/or ribozyme to the targeted microorganism or pathogen. Two separate classes of delivery systems can be manufactured, one biologic in nature and the other abiologic.

5.3.1. Abiologic Delivery Vehicles

Abiologic delivery of one or more toxic agents and/or ribozymes is accomplished by a variety of methods, including packaging plasmid DNA carrying the gene(s) that codes for the toxic agent(s) and/or ribozyme(s) into liposomes or by complexing the plasmid DNA carrying the gene(s) that codes for the toxic agent(s) and/or ribozyme(s) with lipids or liposomes to form DNA-lipid or DNA-liposome complexes. The liposome is composed of cationic and neutral lipids commonly used to transfect cells in vitro. The cationic lipids complex with the plasmid DNA and form liposomes.

A liposome is provided, comprising a nucleic acid comprising a pathogen-specific promoter operably linked to a sequence encoding a tans-acting ribozyme comprising a) a 5' autocatalytically cleaving ribozyme sequence, b) a catalytic ribozyme comprising a target RNA-specific binding site and c) a 3' autocatalytically cleaving ribozyme sequence.

A liposome is provided, comprising a nucleic acid encoding a pathogen-specific promoter operably linked to a sequence encoding one or more toxic agents is provided.

The liposome of the invention, wherein the nucleic acid encodes more than one trans-acting ribozyme and/or more than one toxic agent is provided The liposome can comprise any ribozyme-encoding nucleic acid, or any toxic agent encoding nucleic agent particularly those described herein. Such nucleic acids may be operably linked to a tissue-specific or pathogen-specific promoter.

The liposomal delivery systems of the invention can be used to deliver a nucleic acid comprising a tissue-specific promoter operably linked to a sequence encoding a multi-ribozyme comprising a) a 5' autocatalytically cleaving ribozyme sequence, b) a catalytic ribozyme comprising a target RNA-specific binding site and c) a 3' autocatalytically cleaving ribozyme sequence.

The liposome delivery system of the invention can be used to deliver a nucleic acid comprising a tissue-specific promoter operably linked to a sequence encoding one or more toxic agents. The liposome delivery system of the invention can be used to deliver a nucleic acid comprising a pathogen-specific promoter operably linked to a sequence encoding one or more toxic agents.

Cationic and neutral liposomes are contemplated by this invention. Cationic liposomes can be complexed with a negatively-charged biologically active molecule (e.g., DNA) by mixing these components and allowing them to charge-associate. Cationic liposomes are particularly useful when the biologically active molecule is a nucleic acid because of the nucleic acids negative charge. Examples of cationic liposomes include lipofectin, lipofectamine, lipofectace and DOTAP (Hawley-Nelson et al., 1992, Focus 15(3):73–83; Felgner et al., 1987, Proc. Natl. Acad. Sci. U.S.A. 84:7413; Stewart et al., 1992, Human Gene Therapy 3:267–275). Procedures for forming cationic liposomes encasing substances are standard in the art (Nicolau et al., 1987, Methods Enzymol. 149:157) and can readily be utilized herein by one of ordinary skill in the art to encase the complex of this invention.

In yet another embodiment of the present invention, the plasmid DNA carrying the gene(s) that codes for the toxic agents and/or ribozymes of the invention are complexed with liposomes using an improved method to achieve increased systemic delivery and gene expression (Templeton et al., 1997, Nature Biotechnology 15: 647–652, incorporated herein by reference in its entirety). In accordance with the present invention, an improved formulation of cationic lipids which greatly increase the efficiency of DNA delivery to host cells, with extended half-life in vivo and procedures to target specific tissues in vivo. For example, but not by limitation, peptides and proteins may be engineered to the outer lipid bilayer, such as liver-specific proteins, leads to substantially enhanced delivery to the liver etc.

In one embodiment of the present invention, systemic delivery and in vivo and ex vivo gene expression is optimized using commercially available cationic lipids, e.g., dimethyldioctadeclammonium bromide (DDAB); a biodegradable lipid 1,2-bis(oleoyloxy)-3-(trimethylammonio) propane (DOTAP); these liposomes may be mixed with a neutral lipid, e.g., L-α dioleoyl phosphatidylethanolamine (DOPE) or cholesterol (Chol), two commonly used neutral lipids for systemic delivery. DNA:liposome ratios may be optimized using the methods used by those of skill in the art (e.g., see Templeton et al., 1997, Nature Biotechnology 15: 647–152, incorporated herein by reference in its entirety).

In yet another embodiment of the present invention, the plasmid DNA carrying the nucleic acids encoding the toxic agents and/or ribozymes of the invention may be delivered via polycations, molecules which carry multiple positive charges and are used to achieve gene transfer in vivo and ex vivo. Polycations, such as polyethilenimine, may be used to achieve successful gene transfer in vivo and ex vivo (e.g. see Boletta et al., 1996, J. Am. Soc. Nephrol. 7: 1728, incorporated herein by reference in this entirety.)

The liposomes may be incorporated into a topical ointment for application or delivered in other forms, such as a solution which can be injected into an abscess or delivered systemically, or delivered by an aerosol.

Plasmid DNA coding for the ribozymes or toxic agent is used rather than preformed ribozymes or toxic agent for the following reasons. Plasmid DNA allows the targeted cells to produce the toxic agent or ribozyme and, thus, results in a higher delivered dose to the cell than can be expected by delivery of ribozyme RNA or toxic agent via liposome. The DNA also provides specificity of action based on target sequence specificity. The liposomes deliver their DNA to any cell in the area of administration, including cells of the host. The promoter driving the transcription of the toxic agent or ribozyme is specific for the targeted microorganism and, thus, will be inactive in other cell types. Therefore, liposomal delivery of DNA coding for the toxic agent or ribozyme provides amplification and specificity. The present invention relates to promoter elements which are pathogen-specific or tissue-specific. Such promoter elements are used to achieve pathogen-specific or tissue-specific expression of the toxic agent(s) and/or ribozyme(s) of the present invention. The invention also relates use of an origin of replication which modulates specificity of the replication or copy number of a vector or plasmid in a cell or pathogen.

5.3.2. Biologic Delivery Vehicles

Not all microorganisms are expected to take up DNA delivered by liposome. Consequently, a biologic delivery system is also required. The biologic delivery vehicle of the invention takes advantage of the fact that generalized transducing particles completely lack DNA originating from the viral vector. In one embodiment, such particles only contain sequences of host origin. In other embodiments, such particles contain engineered plasmids/vectors encoding the toxic agent(s) or ribozyme(s) to be delivered. Consequently, the invention uses a biologic assembly of viral head proteins (packaging elements for the antimicrobial therapeutic) around the nucleic acid containing the necessary genetic elements that will insure the desired level of expression of the toxic agent(s) and/or ribozyme(s). An important features of the present invention are the combination of toxic agents or ribozyme with viral delivery and assembly of the virions using a unique combination of plasmid features.

In one preferred embodiment, the invention provides bacteriophage which deliver a toxic agent of the invention. Bacteriophage of the invention may be constructed to deliver one or more toxic agents of the invention, such as one or more toxic gene products, proteins, antisense RNAs, sense RNAs, ribozymes, or combination thereof. In another embodiment of the invention, a host cell is constructed to express a pathogen-specific toxic agent or ribozyme. In yet another embodiment of the invention, a host cell is constructed to express a repressor of a promoter used in the invention.

In other embodiments, a host cell may be engineered to overexpress an antidote to a toxic agent such that the host cell is protected from toxicity and may be used as a producing strain, or manufacturing strain.

The present invention also encompasses expression systems, which may be used to express the toxic agents and/or ribozymes such as bacteriophage, viral vectors, etc. For example, a variety of bacteriophage systems may be utilized to express the selected ribozyme(s) and/or toxic agent(s) of the invention. For example, such bacteriophage systems represent vehicles by which the sequences encoding the toxic agent(s) and/or ribozyme(s) may be introduced into target bacteria both in vivo and in vitro. In several embodiments, the specific bacteriophage which is selected determines the species of bacteria which is targeted and infected by that bacteriophage.

The toxic agents and/or ribozymes of the invention may be used to treat infection from a variety of pathogens. These include but are not limited to microorganisms such as bacteria, parasites, and fungi.

5.3.2.1. Delivery & Expression by Viral Vectors

In accordance with the present invention, a wide variety of viruses and viral vectors may be used to deliver the nucleotide sequences encoding the toxic agent(s) and/or ribozymes of the present invention, a few examples of which are described below. In this regard, a variety of viruses may be genetically engineered to express the selected toxic agent(s) and/or ribozymes in order to target a specific pathogen.

The invention provides for use of a virion which can also be any bacteriophage which specifically infects a bacterial pathogen of the present invention as well as any virus which can be specifically targeted to infect the pathogen of the present invention. For example, the bacteriophage can include, but is not limited to, those specific for bacterial cells of the following genera: Bacillus, Campylobacter, Corynebacterium, Enterobacter, Enterococcus, Escherichia, Klebsiella, Mycobacterium, Pseudomonas, Salmonella, Shigella, Staphylococcus, Streptococcus, Vibrio, Streptomyces, Yersinia and the like (see, e.g., the American Type Culture Collection Catalogue of Bacteria and Bacteriophages, latest edition, Rockville, Md.), as well as any other bacteriophages now known or later identified to specifically infect a bacterial pathogen of this invention. The invention also provides for the use of a virion which specifically infects a fungal pathogen.

This delivery system consists of a DNA plasmid carrying the nucleic acids coding for the toxic agent(s) and/or ribozyme(s) packaged into viral particles. Specificity is conferred by the promoter driving transcription of the toxic agents and/or ribozymes and by the host specificity of the viral vehicle. Specificity is also conferred by the origin of replication controlling vector replication.

In the virions of the present invention, the non-viral DNA can encode one or more toxic agent(s) and/or one or more ribozyme(s). In the virions, the non-viral DNA can comprises a pathogen-specific or tissue-specific promoter operably linked to a sequence encoding one or more toxic agents or ribozymes. In one example the multi-ribozyme may comprise a) a 5' autocatalytically cleaving ribozyme sequence, b) a catalytic ribozyme comprising two target RNA-specific binding sites and c) a 3' autocatalytically cleaving ribozyme sequence. In another example the multi-ribozyme may comprise a) a 5' autocatalytically cleaving ribozyme sequence, b) a nucleic acid sequence encoding a toxic agent and c) a 3' autocatalytically cleaving ribozyme sequence. In a specific embodiement of the invention, the multi-ribozyme comprises a) a 5' autocatalytically cleaving ribozyme sequence, b) a nucleic acid sequence encoding DicF1 and c) a 3' autocatalytically cleaving ribozyme sequence.

The nucleic acid delivered by a virion or liposome can encode one or more toxic agent and/or one or more ribozyme (s) or a combination thereof. The nucleic acid can contain sequences encoding at least two different ribozyme cassettes or at least two different toxic agents. The nucleic acid can contain sequences encoding more than one copy of a multi-ribozyme cassette. The virion can comprise any nucleic acid encoding a ribozyme or toxic agent, particularly those described herein. The nucleic acid can encode at least one or more different ribozyme cassettes. The nucleic acid can encode at least one or more toxic agent. The nucleic acid can encode more than one copy of the same ribozyme cassette or toxic agent. The nucleic acid can encode a cassette in which the cassette is a triple ribozyme. Each ribozyme cassette can contain one or more trans-acting ribozyme(s) or one or more toxic agent(s). The nucleic acid can encode combinations of different ribozymes, or combinations of different toxic agents, some or all of which may be encoded in more than one copy. Additionally, the ribozymes and/or toxic agents may be linked by a short spacer and/or stabilized by a hairpin loop.

The invention provides the use of any virion for the delivery of a toxic agent or ribozyme to a target cell. For example, a common bacteriophage of *E. coli*, P1, is an attractive delivery vehicle for the invention for a number of reasons. First and foremost, P1 has a broad intergenera and interspecies range (Yarmolinsky et al., 1988, Mol. Gen. Genet. 113:273–284). The P1 receptor of *E. coli* is the terminal glucose of the lipopolysaccharide (LPS) core lysergic ring of the bacterial outer membrane (Generalized Transduction, p. 2421–2441. In F. Neidhardt (ed.), Escherichia coli and Salmonella:Cellular and Molecular Biology, 2d ed. Vol.2, ASM Press, Washington, D.C.). Yarmolinsky and Sternberg report that in addition to *E. coli*, this particular phage has the ability to inject its nucleic acid into a large number (>25) of diverse Gram negative bacteria (Yarmolinsky et al., 1988, Mol. Gen. Genet. 113:273–284). Secondly, P1 can accommodate a significant amount of genetic information, over 2% (100,000 bp) of the DNA of *E. coli* (Generalized Transduction, p. 2421–2441. In F. Neidhardt (ed.), *Escherichia coli* and Salmonella:Cellular and Molecular Biology, 2d ed. Vol.2, ASM Press, Washington, D.C.). Consequently, gene dosage of the ribozymes or toxic agents can be increased through multiplication of the toxic agents and/or ribozymes, thereby increasing the microbicidal activity of the toxic agents and/or ribozymes. Additionally, a process utilizing in vitro packaging is also possible. In vitro packaging can be accomplished through the addition of PAC-sites to the genetic information of the toxic agent or ribozyme construct. P1 packaging initiates within one of the P1 PAC genes (Steinberg, N.,1987, J. Mol. Biol. 194(3):469–79). It has been reported that the active PAC site is contained within a 161 base-pair segment of the P1 EcoR1 fragment 20 (Steinberg, N.,1987, J. Mol. Biol. 194(3):469–79). Thus, the phage head serves as a molecular syringe that delivers the inactivating ribozyme(s) and/or toxic agent(s) to the pathogen.

In specific preferred embodiments of the invention, a toxic agent is encoded in a Transfer plasmid, and is used in connection with a P1 bacteriophage delivery system. Such Transfer plasmid preferably contains 1) an origin or replication 2) selectable marker 3) Pac ABC genes with a P1 PAC site 4) P1 lytic replicon and 5) nucleic acids encoding one or more toxic agents of the invention (e.g., antisense molecule, ribozyme, or toxic protein, etc). The Transfer plasmid may be produced in a bacterium producing cell (e.g., a P1 lysogen). In preferred embodiments of the invention, the bacteriophage P1 plasmid (e.g., the P1 prophage) is engineered to be incapable of being packaged into a phage head. In this embodiment, only Transfer plasmids are packaged into virions. Such inhibition of P1 plasmid packaging is accomplished by introducing a mutation or deletion in the P1 plasmid that inhibits the P1 plasmid from being packaged into a virion or phage head. Mutation(s) or deletion(s) of the P1 plasmid which inhibit packaging include but are not limited to one or more mutations and/or deletions in the P1 plasmid PAC site. Any mutation(s) and/or deletion(s) of the P1 plasmid which inhibits packaging of the bacteriophage P1 plasmid is with in the scope of the invention. Such mutations or deletions are introduced by standard techniques known in the art. In several embodiments, the P1 lysogen has a temperature sensitive repressor mutation (e.g. C1.100). Preferably, induction of the P1 lysogen leads to the production of P1 phage heads containing only the packaged Transfer plasmid. Bacteriophage containing the packaged Transfer plasmid nucleic acids may then be used to infect a target cell such as a bacterial pathogen. The bacteriophage infects a bacterial pathogen by injecting its nucleic acids into the bacterium. The toxic agent encoded in the bacteriophage nucleic acids is thus delivered to the bacterium. Within the bacterium, the Transfer plasmid nucleic acids recircularize, and the toxic agent is expressed in the bacterium leading to toxicity and death. Similar mutation and/or deletion strategies may be used with the other viral delivery systems of the invention such that the deletion(s) and/or mutation(s) allow packaging of the nucleic acids encoding toxic agent or ribozyme of the invention, but prevent packaging of nucleic acids encoding one or more viral genes or plasmids. Such strategies allow for construction of viral delivery systems which have increased safety (e.g., when used in connection with therapeutics of the invention).

Another example of a system using bacteriophage virions to package DNA carrying ribozymes and/or toxic agents directed against *E. coli* is the bacteriophage lamda. Similar strategies are used to generate virions capable of delivering ribozymes and/or toxic agents directed against other microorganisms. The virions used to package the DNA can be species-specific, such as the virion derived from the bacteriophage lambda coat, or they can possess a broader host range, such as virion derived from bacteriophage P1, as described above. Broad host-range viruses facilitate production of the antimicrobial agents without the loss of species specificity because species-specific promoters are used to direct the transcription of the ribozymes which are directed against species-specific targeted RNA sequences. For example, a lamda bacteriophage entails the use of a plasmid carrying the ribozyme and/or toxic agent, a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of replication on the plasmid and all of the structural components needed to form mature virions; however, the lysogen is not able to replicate and package its own DNA into the virions. The lysogen may also carry a temperature-sensitive repressor mutation (such as the cI857).

Retroviral vectors are also commonly used to deliver genes to host cells both in vivo and ex vivo. Retroviral vectors are extremely efficient gene delivery vehicles that cause no detectable harm as they enter the cells. The retroviral nucleic acid may integrate into host chromosomal DNA allowing for long-term persistence and stable transmission to future progeny, such a vector would be useful for the delivery of a toxic agent and/or ribozyme(s) used to target a cellular gene product involved in a chronic or hereditary disorder or to target a viral gene or a microbial gene or a parasitic gene involved in a chronic or persistent infection. An example of an appropriate retroviral vector are, lentiviruses which have the advantage of infecting and transducing non-dividing cells. In such an embodiment, a lentiviral vector encoding a packagable RNA vector genome operably linked to a promoter in which all the functional retroviral auxiliary genes are absent, is used to transfer the DNA encoding the toxic agent and/or ribozyme of the present invention. Examples of such vectors are described in WO 98/17815, WO 98/17816 and WO 98/17817, each of which is incorporated herein by reference in their entirety.

In yet another embodiment, non-integrating viral vectors which infect and transduce non-dividing cells, such as adenoviral vectors may be used to deliver the toxic agent and/or ribozymes of the present invention. Adenoviral vectors have several advantages because the use of such vectors avoids risks associated with permanently altering the host cell genome or of promoting insertional mutagenesis. Adenoviruses are one of the best developed non-integrating viral vectors and can be used to transfer expression cassettes of up to 75 kb. Recombinant adenoviruses can be produced at very high titers, is highly infectious and efficiently transfers genes to a wide variety of non-replicating and replicating cells and is ideal for in vivo mammalian gene transfer.

Adenovirus-based vectors are relatively safe and can be manipulated to encode the desired toxic agent and/or ribozymes and at the same time to be inactivated in terms of their ability to replicate in a normal lytic viral life cycle. Adenovirus has a natural tropism for airway epithelia. Therefore, adenovirus-based vectors are particularly preferred for respiratory gene therapy applications. In a particular embodiment, the adenovirus-based gene therapy vector comprises an adenovirus 2 serotype genome in which the E1a and the E1b regions of the genome, which are involved in early stages of viral replication have been deleted and replaced by nucleotide sequences of interest. In a further embodiment, the adenovirus-based gene therapy vector contains only the essential open reading frame (ORF3 or ORF6 of adenoviral early region 4 (E4) and is deleted of all other E4 open reading frames, or may additionally contain deletions in the E3 regions (e.g., see U.S. Pat. No. 5,670,488, incorporated herein by reference in its entirety). In another embodiment, the adenovirus-based therapy vector used may be a pseudo-adenovirus (PAV), which contain no harmful viral genes and a theoretical capacity for foreign material of nearly 36 kb.

In another embodiment, adeno-associated virus (AAV) systems may be used to deliver the toxic agent and/or ribozymes of the present invention. AAV has a wide host range and AAV vectors have currently have been designed which do not require helper virus. Examples of such AAV vectors are described in WO 97/17458, incorporated herein by reference in its entirety.

Vaccinia viral vectors may be used in accordance with the present invention, as large fragments of DNA are easily cloned into its genome and recombinant attenuated vaccinia variants have been described (Meyer, et al., 1991, J. Gen. Virol. 72:1031–1038). Orthomyxoviruses, including influenza; Paramyxoviruses, including respiratory syncytial virus and Sendai virus; and Rhabdoviruses may be engineered to express mutations which result in attenuated phenotypes (see U.S. Pat. No. 5,578,473, issued Nov. 26, 1996). These viral genomes may also be engineered to express foreign nucleotide sequences, such as the selected toxic agent and/or ribozymes of the present invention (see U.S. Pat. No. 5,166,057, issued Nov. 24, 1992, incorporated herein by reference in its entirety). Reverse genetic techniques can be applied to manipulate negative and positive strand RNA viral genomes to introduce mutations which result in attenuated phenotypes, as demonstrated in influenza virus, Herpes Simplex virus, cytomegalovirus and Epstein-Barr virus, Sindbis virus and poliovirus (see Palese et al., 1996, Proc. Natl. Acad. Sci. USA 93:11354–11358). These techniques may also be utilized to introduce foreign DNA, i.e., the selected toxic agent and/or ribozyme, to create recombinant viral vectors to be used in accordance with the present invention. In addition, attenuated adenoviruses and retroviruses may be engineered to express the toxic agent and/or ribozymes. Therefore, a wide variety of viruses may be engineered to design the ribozymes delivery vehicles of the present invention.

The viral vectors of the present invention may be engineered to express the toxic agents and/or ribozymes in a tissue specific manner. For example, the promoter of the carcinoembryonic antigen (LEA) is expressed in a proportion of breast, lung and colorectal cancers, but rarely in healthy tissues. In order to target a hepatoma, the α-fetoprotein (AFP) promoter whose activity is restricted to malignant cells. Proliferating cells can be targeted with a flt-1 promoter, which has been shown to allow preferential targeting of proliferating endothelial cells. See Miller et al., 1997, Human Gene Therapy 8:803–815, incorporated herein by reference in its entirety.

5.3.2.2. Delivery & Expression Using Multi-Ribozymes

In another embodiment of the invention, expression of a toxic agent is directed by a tissue-specific, pathogen-specific, and/or target-specific ribozyme or ribozyme cassette. The invention provides ribozymes that have the unique characteristic of being both target RNA-specific in their catalytic action, and tissue-specific or pathogen-specific in their expression. A ribozyme can be tissue-specific in the case of treating tissue-specific disease, or it can be pathogen-specific in the case of treating a pathogen such as *E. coli*. Multi-ribozymes may have one or more target-specific ribozyme(s) (e.g., a trans-acting catalytic ribozyme) as well as elements which control tissue-specific or pathogen-specific expression.

In one embodiment, the nucleic acids of the invention comprise a tissue-specific promoter operably linked to a sequence encoding a) a 5' autocatalytically cleaving ribozyme sequence, b) a catalytic ribozyme comprising a target RNA-specific binding site and c) a 3' autocatalytically cleaving ribozyme sequence.

The tissue-specific promoter in the ribozyme-producing construct results in tissue-specific expression of the ribozyme in tissue(s) that actively transcribe RNA from the selected promoter. Thus, only the target RNA in tissue that utilize the promoter will be cleaved by the ribozyme.

Further, in accordance with the present invention, the multi-ribozyme may consist of one or more ribozyme cassettes. Each cassette in turn may consist of a catalytic core and one or more flanking sequences. In one embodiment, the ribozyme cassette may consist of a 5' autocatalytically cleaving ribozyme sequence, a core catalytic ribozyme comprising a trans-acting ribozyme and a 3' autocatalytically cleaving ribozyme. In yet another embodiment, the catalytic core contains sequences encoding one or more toxic agent (s). In other embodiments, the multi-ribozymes comprise a cassette including, the enhanced 5' and 3' autocatalytically cleaving ribozyme sequence. In another embodiment, the multi-ribozymes contain one or more internal trans-acting ribozymes. In a preferred embodiment, the multi-ribozymes of the present invention include, but are no limited to triple ribozyme cassettes. In another embodiment, multi-ribozymes include but are not limited to one or more triple ribozyme cassettes linked together. In yet another embodiment, the multi-ribozyme comprises a ribozyme cassette containing one or more internal trans-acting ribozyme. In an additional embodiment, the multi-ribozyme comprises a series of one or more ribozyme cassettes containing one or more internal trans-acting ribozymes or any combination thereof. In further embodiments, the multi-ribozyme cassettes or toxic agent(s) are expressed in a tissue-specific or pathogen-specific manner. In a preferred embodiment of the invention, pathogen-specific expression is coupled to a pathogen-specific promoter.

5.4. Promoter Selection

Promoter selection is accomplished using techniques that are available in the art. As used herein, regulatory elements include but are not limited to, inducible and non-inducible promoters, enhancers, operators and other elements known to those skilled in the art that drive and regulate expression. Specifically, the invention provides inducible promoters which have increased transcriptional control and high expression levels. The promoter can be a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of toxic agent or ribozyme expression in the targeted microbe.

Promoters specific for the target (e.g., a specific pathogen, genus, etc.) in question can be selected by screening genomic sequences for the ability to activate a promoterless reporter gene. The promoterless reporter gene is based on the strategy developed for use with plasmid pMC1871 (Casadaban et al., 1983, Meth. Enzymol. 100:293). For non-viral pathogens, plasmid capable of stable replication and maintenance in the microorganism understudy is modified by standard molecular biology techniques to carry the coding region of a reporter gene (Sambrook et al. latest edition). The reporter gene can be any of a number of standard reporter genes including but not limited to the lacZ gene of *E. coli*, which codes for β-galactosidase. Total genomic DNA is isolated from cells of the pathogen, cleaved with restriction endonucleases to yield fragments of a few hundred basepairs on average. These fragments are then ligated into a unique restriction endonuclease cleavage site at the 5' end of the reporter gene coding region, creating a library of plasmids. The library is then transformed into the pathogen by standard techniques and the resulting transformants are screened for expression of the reporter gene. In the case of lacZ, the transformants can be plated onto medium containing the chromogenic galactosidase substrate X-Gal (5-bromo-4-chloro-3-indolyl-D-galactoside). Transformants that contain a plasmid with an insert carrying a promoter will express β-galactosidase and will turn blue on X-Gal plates. The intensity of the blue color is relative to the level of expression; promoters of different strength can be selected based on the intensity of the blue color.

The above-described screening procedure can be modified to identify regulated promoters. For example, promoters that are regulated by carbon source availability can be screened on plates that contain different carbon sources. Other modifications are possible and will depend, in part, on the organism in question. To test for species-specificity, the identified promoters are transferred to promoterless reporter plasmids capable of replication and maintenance in a different organism. Truly species-specific or pathogen-specific promoters will not activate the expression of the reporter gene in any other species. Obvious modifications can be used to identify and test artificial promoters composed of synthetic oligonucleotides inserted into the promoterless reporter plasmid.

In one embodiment, the nucleic acids of the invention comprise a tissue-specific promoter operably linked to a sequence encoding a 5' autocatalytically cleaving ribozyme sequence, one or more catalytic target-specific trans-acting ribozymes or one or more toxic agents and a 3' autocatalytically cleaving ribozyme sequence.

The tissue-specific promoter in the ribozyme-producing construct results in tissue-specific expression of the ribozyme in tissue(s) that actively transcribe RNA from the selected promoter. Thus, only the target RNA in tissue that utilize the promoter will be cleaved by the ribozyme. The pathogen-specific promoter binding site in the ribozyme-producing construct results in pathogen-specific expression of the ribozyme in pathogens or microbes that actively transcribe RNA from the selected promoter. Thus, only the target RNA in pathogens that utilize the promoter will be cleaved by the ribozyme.

Tissue-specific promoters can be used in the present nucleic acid constructs. Examples of these promoters include the sequences for probasin-promoter, a promoter-specific for prostate epithelium prostate-specific antigen (prostate), keratin, k7 (epidermal sabaceus glands), albumin (liver), fatty acid binding protein (ilium), whey acidic protein (breast), lactalbumin, smooth muscle actin (smooth muscle), etc. It will also be clear that target-specific promoters not yet identified can be used to target expression of the present ribozymes to the selected tissue(s). Once a target-specific promoter is identified its binding sequence can be determined by routine methods such as sequence analysis may be used. The promoter is defined by deletion analysis, mutagenesis, footprinting, gel shifts and transfection analyses (Sambrook et al., *Molecular Cloning: A Laboratory Manual*, 2nd Ed., Cold Spring Harbor Laboratory, Cold Spring Harbor, N.Y., 1989). Pathogen-specific promoters can be used in the present nucleic acid constructs.

5.4.1. Bacterial Specific Promoters/Expression

The present invention provides bacterial promoters that allow for tight regulation of transcription and enhanced expression. In one embodiment, a novel promoter called LEASHI has been constructed from three elements (see FIG. 1). The first element, termed RIP is a combination of two consensus sites at −10(TATAAT) and −35(TTGACA) located with respect to transcription initiation. The second element is based on the lacI repressor binding sequence (termed lac operator sequence) which is placed between the −10 and −35 consensus sites. This is in contrast to the conventional lac and tac promoters where the lac operator is found downstream of the −10 consensus element. Placement of the lac operator between the −10 and −35 sites, more effectively blocks RNA polymerase binding to the promoter, thus enhancing transcriptional control from the promoter. Thus, the levels of lacI repressor protein present, which binds to the operator sequence and hence determines the rate of transcription, are controlled in two ways; 1) by endogenously expressed lacI protein and 2) by a plasmid expressing the lacI gene. Under normal conditions, the lacI repressor protein binds to the lac operator sequence and prevents transcription by blocking RNA polymerase binding. The promoter is 'switched on' following the addition of isopropyl B-D-thiogalacto pyranoside, which binds and subsequently titrates out the repressor protein. RNA polymerase can then bind to the promoter and transcription can proceed.

The third element of the LEASHI promoter is termed the UP element. The UP element is an adenine/thymine rich sequence which is placed immediately upstream of the −35 element. Addition of the UP element, further increases expression from this promoter.

Classical bacterial inducible promoters are renowned for their inability to tightly control transcription, and a significant level of background expression is characteristically observed. A significant advantage of the promoter of the present invention is that it will alleviate the high levels of background commonly observed in inducible promoters. A limiting factor leading to high background levels of transcription when a promoter of interest is on a high-copy number plasmid is due to the lack of repressor molecules available to bind to the promoters. The present invention overcomes this problem by using a lacI expression plasmid and secondly, by placement of the lac operator between the −35 and −10 consensus elements which more effectively blocks transcription during normal conditions. Furthermore, the UP element placed immediately upstream of the −35 region enhances transcription from the core promoter.

In a specific embodiment of the invention, the promoter which is operably linked to a nucleic acid encoding a toxic agent or ribozyme is the LEASHI promoter.

In specific embodiment, a ribozymes of the invention is operably linked to a LEASHI promoter. In another specific embodiment of the invention, a toxic agent of the invention is operably linked to a LEASHI promoter.

In a specific embodiment, the invention encompasses expression of DicF1 from a ribozyme cassette under the control of a regulatable promoter, such as the LEASHI promoter.

In another embodiment of the invention, the lacI operator sequence of the LEASHI promoter is placed 5' of the −35 consensus site. In another embodiment of the invention, the lacI operator sequence of the LEASHI promoter is placed 3' of the −10 consensus site. In other embodiment of the invention, one or more additional lacI operator sequences are added to the LEASHI promoter and are placed 5' to the −35 consensus site and/or 3' of the of the −10 consensus site.

The invention also relates to the rrnB promoter. In one embodiment of the invention, the promoter is the rrnB promoter is modified such that one or more lacI operator sites are added to the promoter. An example of such a modified rrnB promoter is shown in FIG. 1B. In another embodiment of the invention, the lacI operator sequence of the rrnB promoter is placed 3' of the −10 consensus site. In other embodiment of the invention, one or more additional lacI operator sequences are added to the rrnB promoter and are placed 5' to the −35 consensus site and/or 3' of the of the −10 consensus site.

5.5. Host Cells

The present invention encompasses the expression of the toxic agents and/or ribozymes in primary cells, animal, insect, fungal, bacterial, and yeast cells for in vitro screening assay and ex vivo gene therapy. The present invention also encompasses the expression of the toxic agents and/or ribozymes in cell lines for in vitro screening assay and ex vivo gene therapy. In accordance with the present invention, a variety of primary or secondary cells or cell strains may be used including but not limited to cells isolated from skin, bone marrow, liver, pancreas, kidney, adrenal and neurological tissue to name a few. Other cell types that may be used in accordance with the present invention are immune cells (such as T-cells, B-cells, natural killer cells, etc.), macrophages/monocytes, adipoctyes, pericytes, fibroblasts, neuronal cells, reticular cells etc. In a further embodiment, secondary cell lines may be used as engineered responsive cells and tissues in accordance with the present invention, including, but not limited to hepatic cell lines, such as CWSV, NR, Chang liver cells, or other cell lines such as CHO, VERO, BHK, Hela, COS, MDCK, 293, 373, HUVEC, CaSki and W138 cell lines. A toxic agent or ribozyme of the invention may also be expressed in any cell line which is not sensitive to the effects of the toxic agent or ribozyme (e.g., a cell which is resistant to the particular toxic agent or ribozyme, or a cell which co-expresses a neutralizing agent or antidote).

For long term, high-yield production of recombinant proteins, stable expression is preferred. For example, cell lines which stably express the selected toxic agent and/or ribozyme may be engineered. When a toxic agent is to be stably expressed, expression may be controlled by an inducible promoter, or, the cell may be engineered to co-express an antidote to the toxic agent, in order to allow the cell to survive during production of a toxic agent. Rather than using expression vectors which contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to grow to form foci which in turn can be cloned and expanded into cell lines. This method may advantageously be used to engineer cell lines. This method may advantageously be used to engineer cell lines which express the selected gene products. Such cell lines would be particularly useful in screening and evaluation of compounds that affect the endogenous activity of the selected gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

5.6. Targets

The toxic agents of the present invention may be engineered to target essential genes, gene products, or processes necessary for growth of parasites, bacteria, virus life cycles, etc., and expression can be driven with tissue-specific or pathogen-specific promoters. The toxic agents or trans-acting catalytic ribozymes of the present invention may be engineered to target a wide variety of cellular RNAs, tumor or cancer associated with RNAs, bacterial RNAs, parasitic RNA etc. The toxic agent or trans-acting ribozyme can be targeted to noncellular RNAs necessary for growth of parasites, bacteria, virus life cycles, etc., and expression can be driven with tissue-specific or pathogen-specific promoters.

The virion construct used in this method can comprise any nucleic acid encoding a toxic agent or ribozyme, particularly those described herein targeted to essential genes of the pathogen or diseased cell. The virion can be a bacteriophage, or other virus selected for its ability to target a specific cell-type, microorganism or animal. The bacteriophage can be lambda, P1 or other phage. When P1 is the virion, the Tranfer plasmid can further comprise a PAC site and PAC ACB genes. This construct is preferred when using P1. Alternatively, the virion can be selected because it has a broad range of targets. Important examples which are specifically presented in the application are:

A) Use of the LEASHI promoter with a Bacterial target (such as *E. coli*) to direct expression of the toxic agent such as Doc, Gef, or DicF1;

B) Use of the LEASHI promoter with a Bacterial target (such as *E. coli*) to direct expression of the toxic agent comprising Sof sense RNA;

C) Use of the albumin promoter with a Hepatitis B virus target (chosen to cleave the viral RNA pregenome, S protein, and polymerase/and x protein transcripts using the same ribozyme target site);

D) Use of generic promoters active in erythrocytes, using a ribozyme targeted to highly conserved regions of the EMP-1 protein family from *P. falciparum*, which are necessary for cytoadherence and antigenic variation in malaria; and E) Use of the keratin 7 promoter, with trans-acting ribozymes targeted to a specific sites near the translational start site of the E6 protein, a site known to be critical for expression of both the E6 and E7 proteins which are intimately involved in cervical carcinogenesis, as well as a more 3' site in a highly conserved region of the E6 protein.

Examples of bacterial pathogens that can be targeted by a toxic agent or multi-ribozyme construct of the present invention include, but are not limited to, species of the following genera: Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae, as well as bacterial species such as: *P. aeruginosa; E. coli, P. cepacia, S. epidermis, E. faecalis, S. pneumonias, S. aureus, N. meningitidis, S. pyogenes, Pasteurella multocida, Treponema pallidum,* and *P. mirabilis.*

The pathogen of the present invention can also include, but is not limited to pathogenic fungi such as *Cryptococcus neoformans; Blastomyces dermatitidis; Aiellomyces dermatitidis; Histoplasma capsulatum; Coccidioides immitis;* Candida species, including *C. albicans, C. tropicalis, C. parapsilosis, C. guilliermondii* and *C. krusei,* Aspergillus species, including *A. fumigatus, A. flavus* and *A. niger,* Rhizopus species; Rhizomucor species; Cunninghammella species; Apophysomyces species, including *A. saksenaea, A. mucor* and *A. absidia; Sporothrix schenckii, Paracoccidioides brasiliensis; Pseudallescheria boydii, Torulopsis glabrata;* Trichophyton species, Microsporum species and Dermatophyres species, as well as any other yeast or fungus now known or later identified to be pathogenic.

Furthermore, the pathogen of the present invention can be a parasite, including, but not limited to, members of the Apicomplexa phylum such as, for example, Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus and Gregarina spp.; *Pneumocystis carinii;* members of the *Microspora phylum* such as, for example, Nosema, Enterocytozoon, Encephalitozoon, Septata, Mrazekia, Amblyospora, Ameson, Glugea, Pleistophora and Microsporidium spp.; and members of the *Ascetospora phylum* such as, for example, Haplosporidium spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T saginata, Trichomonas vaginatis, T. hominis, T. tenax; Giardia lamblia; Cryptosporidium parvum; Pneumocytis carinii, Babesia bovis, B. divergens, B. microti, Isospora belli, L. hominis; Dientamoeba fragilis; Onchocerca volvulus; Ascaris lumbricoides; Necator americanis; Ancylostoma duodenale, Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchisfelineas, G. Viverini, Fasciola hepatica, Sarcoptes scabiei, Pediculus humanus; Phthirlus pubis;* and *Dermatobia hominis,* as well as any other parasite now known or later identified to be pathogenic.

Examples of viral pathogens include, but are not limited to, retroviruses (human immunodeficiency viruses), herpes viruses (herpes simplex virus; Epstein Barr virus; varicella zoster virus), orthomyxoviruses (influenza), paramyxoviruses (measles virus; mumps virus; respiratory syncytial virus), picorna viruses (Coxsackie viruses; rhinoviruses), hepatitis viruses (hepatitis C), bunyaviruses (hantavirus; Rift Valley fever virus), arenaviruses (Lassa fever virus), flaviviruses (dengue fever virus; yellow fever virus; chikungunya virus), adenoviruses, birnaviruses, phleboviruses, caliciviruses, hepadnaviruses, orbiviruses, papovaviruses, poxviruses, reoviruses, rotaviruses, rhabdoviruses, parvoviruses, alphaviruses, pestiviruses, rubiviruses, filiviruses, coronaviruses, as well as any virus of the family of picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae, and any other virus now known or later identified to be pathogenic.

5.7. Target Selection

One critical component in the development of the therapeutics of the invention is the selection of appropriate targets. For ribozymes to be effective anti-microbial therapy, it is preferable to target the RNA of, for example, several key proteins, tRNA, rRNA or any other RNA molecule essential for cell viability or fitness, in order to insure complete inactivation and prevent escape of the invading microorganism. For example, several bacterial genes, essential for viability and unrelated in activity, have been selected and are described herein to highlight how the selection of appropriate mRNA targets is carried out for the preferred construction of the antimicrobial agent against prokaryotic targets. Cross-genera RNA targets can be used to design an antimicrobial that can have broad application, modified by the specificity of the promoter. In addition, several toxic agents are described herein to highlight how the selection of appropriate toxic agents is carried out for the preferred construction of the antimicrobial agent against prokaryotic targets.

In one embodiment of the invention, the first ribozyme targets an essential transcription factor, the second ribozyme targets an essential general secretory component, the third ribozyme targets an essential component of the primosome required for DNA biosynthesis and the fourth ribozyme targets an enzyme required for cell division. Consequently, the ribozymes are redundant in the fact that they inhibit growth by specifically targeting a fundamental process required for bacterial growth. Thus, this can minimize the development of resistance to the antimicrobial therapeutic.

The first gene, rpoA, produces an essential protein, rpoA or the alpha subunit of RNA core polymerase. rpoA was selected rather than the other components of the RNA polymerase holoenzyme, because it is thought to facilitate the assembly of an active RNA polymerase enzyme complex. Inactivation of the rpoA transcript results in a decrease in the intracellular concentration of the holoenyme RNA polymerase rendering the cell less able to respond to changes demanded of it once it has invaded a new host. The nucleotide sequence of rpoA is known for a large number of microorganisms (>20 genera) and they are readily available from GenBank.

The second ribozyme target can be the mRNA of the secA gene from bacteria. The product of this gene is the essential and rate-limiting component of the general secretory pathway in bacteria (Bassford et al., 1994, Nucleic Acids Reseaarch April 11, 22(7):1326; Nucleic Acid Research. 22(3):293–300). SecA has been found in every prokaryotic cell investigated to date. Additionally, its biosynthesis is translationally coupled to the upstream gene, X (Schmidt et al., 1991, J. Bacteriol. 173(20):6605–11), presenting a convenient target for a ribozyme. Inhibition or decreased synthesis of secA is also sufficient to confer a reduction in viability to the cell (Schmidt et al., 1987, J. Bacteriol. 171(2):643–9). Furthermore, as a pathogen responds to changes required of the infectious process a change in the availability of a key protein such as secA will disadvantage the pathogen enabling the host to counteract it. Finally, control over the secretion-responsive expression of secA is at the level of translation (Christoffersen et al., 1995, J. Med. Chem. 38(12):2023–37), and the regulatory sequences within its polycistronic message have been localized to a region comprised of the end of the upstream gene, X, and the beginning of secA. Consequently, inactivation of the transcript by the catalytic cleavage of a ribozyme has profound consequences for the viability of the invading microorganism.

The third ribozyme can target an essential factor for DNA biosynthesis, DnaG. Every 1 to 2 seconds, at least 1,000 times for each replication fork within $E.\ coli$, priming of an Okazaki fragment is repeated as a result of an interaction between the cellular primase dnaG (Boucbe et al., 1975, J. Biol. Chem. 250:5995–6001) and dnaB (Marians, K. J. 1996, Replication Fork Propagation, p. 749–763. In F. C. Neidhardt (ed.), $Escherichia\ coli$ and Salmonella: Cellular and Molecular Biology, 2nd ed, vol. 1. American Society for Microbiology, Washington, D.C.). As would be expected of a protein required every 1 to 2 seconds during replication, a lesion within DnaG or an alteration in its concentration results in an immediate stop phenotype (Marians, K. J. 1996, Replication Fork Propagation, p. 749–763. In F. C. Neidhardt (ed.), $Escherichia\ coli$ and Salmonella: Cellular and Molecular Biology, 2nd ed, vol. 1. American Society for Microbiology, Washington, D.C.); Weschler et al., 1971, Mol. Gen. Genet. 113:273–284). Therefore, inactivation of the DnaG message by a ribozyme should have profound cellular consequences in that general priming of the lagging strand is reduced if not eliminated. DnaG is a component of the primosome, a multi-protein complex responsible for priming replication. Any of the components of the primosome, either individually or in any combination, can serve as a target for inactivation of the primosome and, thus, kill the cell. The other components of the primosome are DnaB, DnaC, DnaT, PriA, PriB, and PriC. Thus, the primosome is also sufficiently complex to provide numerous other targets (DnaB, DnaC, DnaT, PriA, PriB and PriC) for inactivation by the trans-acting ribozyme.

The fourth target can be ftsZ. This gene also encodes an essential protein, ftsZ, that is required for cell division in that it is responsible for the initiation of separation. ftsZ was selected because cleavage of the ftsZ RNA leads to inhibition of cell division and a reduction in viability. Any toxic agent or ribozyme which targets ftsZ (such as DicF1) may be used to inhibit division of a cell requiring the ftsZ gene product. Also, for example, upon cleavage of the ftsZ message by a ribozyme, such ribozyme can attack additional copies of the ftsZ message inhibiting the division of the cell. The nucleotide sequence of ftsZ like the other targets selected, is commonly available from GenBank.

It should be clear that any other essential protein of a pathogen can have its message targeted in the present invention, and that determining which proteins are essential can be routinely determined according to standard protocols in the art. In fact, there are over 52,000 viral, 41,000 bacterial and 12,300 fungal sequences deposited in the public section of the Entrez Database at the National Center for Biotechnology Information. Any of these can be used to design the catalytic trans-acting ribozyme of the invention.

In addition to targeting mRNA of essential proteins ribozymes may be targeted against other RNA species within the cell. Specifically, appropriate targets in bacteria, fungi and other lower eukarytoes include ribosomal RNA such as Small Subunit RNAs (SSU) or Large Subunit (LSU) and tRNA molecules required for protein synthesis. With respect to pathogenic Staphlococus, the RNA III moiety in a relatively low abundance transcript which is not translated and should be accessible for cleavage. As long as the RNA targeted contains a canonical ribozyme cleavage domain, the ribozyme therapeutic can hybridize and cleave the complementary RNA, thus impacting the fitness of the microbial cell. Additionally, over 3000 rRNA species have been sequenced and aligned. This information is available from the Ribosomal Database Project and should facilitate rapid design and adaptation of ribozyme(s) against such targets. For example the 16S rRNA molecule of bacteria is especially attractive in that there are over 4000 copies of the 16S rRNA per cell. Consequently, a reduction in number slows the process of protein synthesis in so far as the 16S rRNA molecule is involved in the process of translational initiation. Thus, a toxic agent or ribozyme directed against mRNA and rRNA impacts the fitness of the offending microorganism.

In another embodiment of the inventions toxic agents are selected based on their ability to inhibit the growth of a pathogen or selected cell or cause lethality in a pathogen or selected cell. Several specific examples of toxic agents are described herein which serve to illustrate the selection of a toxic agent of the invention.

First, a toxic agent may be an addiction system toxin (such as doc). Doc encodes a toxin which is translationally coupled to a protein called phd. Phd is an antidote to doc, and acts to neutralize the toxic effects of doc. The two proteins, phd and doc form an operon on the P1 plasmid in which phd precedes doe. Further, the phd gene contains a ribosome entry site and is translated efficiently. The native doc gene however, lacks a recognizable ribosome entry site and is translated poorly. Thus, doc was selected because of its potential toxicity when expressed in a cell or pathogen lacking the corresponding antidote, phd. In this embodiment, doc has been engineered to be uncoupled from phd. For example, doc is engineered into a separate plasmid from phd. The plasmid containing doc has also been engineered such that a ribosome entry site has been constructed upstream of the nucleic acids encoding doc in order to increase the levels of translation of doc. This plasmid is containing the toxic agent and/or ribozyme of the invention is called the Transfer plasmid. In one specific embodiment of the invention, the Transfer plasmid encodes the toxic agent doc.

A packaging strain (e.g., bacteria cell) is then used to package the Transfer plasmid containing doc into a bacteriophage phage head. The packaging strain cells contain the P1 plasmid as well as the Transfer plasmid with the uncoupled doc and ribosome entry site. The packaging strain may also include a third plasmid, if necessary, which encodes additional phd protein which can act to protect the packaging strain against the toxicity of doc (e.g., if the promoter of the Transfer plasmid is leaky and leads to production of doc in the packaging cell).

Thus, the packaging strain acts to package the transfer plasmid containing the toxic agent (such as doc) into phage heads or virions. Phage lysates of the packaging strain contain the infectious bacteriophage virions.

The phage lysates are then used to infect a selected pathogen (e.g., *E. coli, P. aerugunosa*, etc.). Further, the phage lysate may be used to prepare a therapeutic of the invention. Phage may be delivered to a bacteria or pathogen or a host with a pathogenic infection by methods described herein, or by any method known in the art. For example, the phage lysates may be lyophilized and delivered to a host in need of treatment for a bacterial infection, fungal infection, etc.

The above targeting method, wherein the virion is a bacteriophage is provided. The bacteriophage can be lambda, P1 or other phage. The targeting method, wherein the Transfer plasmid further comprises a PAC site and PAC ABC genes is also provided. The bacteriophage P1 which is engineered to be packaging deficient is also provided. This construct is preferred when using P1.

Second, a toxic agent of the invention may be an antisense molecule selected to target an antidote of a toxic protein, or selected to target an essential RNA critical to the survival of a pathogen or selected cell. The proposed target of the toxic antisense molecule of the invention may also be the RNA of any gene which plays a critical role in the survival of the pathogen, or which is essential to the pathogen's life cycle. The present invention also encompasses modifications to naturally occurring antisense molecules which modulate the expression of an essential gene product of a pathogen. For example, as described below, one proposed target of an antisense of the invention is the ftsZ gene whose gene product plays a critical role in the initiation of cell division of *E. coli*. For example, the toxic agent may be an antisense molecule which is constructed to be modified and enhanced such that is it more homologous to its target RNA. Thus, as in the case of DicF, the antisense sequence has been modified and enhanced to engineer the DicF1 antisense toxic agent, which has increased complementarity to its target RNA. Further, the DicF1 or DicF1-like antisense molecule has enhanced properties in that it may be expressed and delivered by the methods of the invention, thus providing the target cell with increased levels of the toxic antisense RNA.

Third, a toxic agent may be selected to target an essential antisense molecule. Thus, a toxic agent may be a sense molecule which is designed to be complementary to an essential antisense RNA. An example of an essential antisense molecule is Sof. Sof is an antisense antidote for the chromosomally encoded toxin called Gef (Poulsen, L., et al., 1991, Mol. Microbiology 5:1639–48). Sof normally acts to regulate the levels of Gef in the bacterium. The inventors of the present invention have designed sense molecules which are complementary to Sof. The sense molecules against Sof act to inhibit the ability of Sof to regulate Gef, and thus cause toxicity in the pathogen by allowing the endogenous Gef levels to become toxic.

5.8. Protection of Toxic Agent and/or Ribozyme Producing Cells

The nucleic acids coding for the toxic agents or ribozymes can be toxic to the cells that are needed to produce the toxic agent or ribozyme-carrying virions. When using a broad host-range virus like P1, the organism used to produce the virion can be different from the target organism. In this way, the producing strain is resistant to the toxic effects of the toxic agents or ribozymes because they are not efficiently expressed in the producing strain, due to species-specific promoter elements, and the ribozymes will not have any target RNA molecules to attack, due to the species-specific sequences that target the ribozymes. When using a species-specific virus that must be expressed and assembled within a strain of the targeted microorganism, this toxicity becomes a significant concern. The assembly of a virion consisting of anti-*E. coli* ribozyme or toxic agent genes packaged in lambda will illustrate the approach used to circumvent the toxicity. For example, the ribozymes directed against RNA species of E. coli is expressed from an artificial promoter containing consensus promoter elements. This promoter provides high level transcription of the ribozyme immediately upon infection of targeted cells. In order to prevent the unwanted death of the producing strain of E. coli, transcription is repressed in the producing strain by a mechanism not available to the wildtype strains that are targeted for killing. Sequences constituting the DNA binding sites for a heterologous transcription factor are interspersed between the essential activating elements of the ribozyme promoter. Expression of the heterologous transcription factor in the producing strain results in the occlusion of the activating promoter elements and preventing the binding of RNA polymerase. As an example, the gene for the Saccharomyces cerevisiae transcription factor Ste12p may be expressed in E. coli and bind to its binding sites, the pheromone response element, located within the ribozyme promoter. Ste12p will not be found in wild strains of E. coli; therefore, the ribozyme promoter will be accessible to RNA polymerase following delivery of the plasmid to the targeted cells.

An alternative strategy that can protect the producing strain from the toxicity of the ribozymes employs ribozyme-resistant versions of the targeted RNA molecules. This strategy can be used when the target RNA molecule codes for a protein. The ribozyme target site within the mRNA molecule is mutated by site-directed mutagenesis such that the amino acid sequence of the translated protein does not change but the mRNA sequence no longer serves as a substrate for the ribozyme. For example, hammerhead ribozymes require an NUX sequence within the target mRNA for cleavage to occur. By changing this sequence to something else, the ribozyme will not cleave the mRNA. This type of ribozyme resistant version of the target RNA can be expressed from a plasmid or integrated into the chromosome of the producing strain and thus render this strain resistant to the toxic effects of the ribozyme.

Another strategy that can protect the producing cell from the toxicity of a toxic agent employs co-expression of a neutralizing agent or antidote. Such co-expression of an antidote or neutralization agent protects the packaging cell from the toxic effects of the encoded toxic agent. Such a strategy is particularly useful is the promoter used to express the toxic agent is leaky, and leads to expression of the toxic agent in the producing cell. For example, a packaging strain (e.g., bacteria cell) may used to package the a viral vector containing a toxic agent into a bacteriophage phage head. Survival of the packaging cell or optimization of the quantities of vector or phage made by the producing cell may require co-expression of an antidote or neutralization agent in the producing cell. A neutralization agent is any molecule (such as protein, antisense, sense, or other molecule (such as a drug, chemical, etc.)) which counteracts the toxic effects of a toxic agent. By way of illustration, in a specific example, the packaging strain cells contain a bacteriophage P1 plasmid as well as the Transfer plasmid comprising the toxic agent doc and a ribosome entry site. In the case that the Transfer plasmid is determined to be toxic to the packaging strain, a third plasmid may be introduced, which encodes an antidote to doc, such as the phd protein. The additional plasmid with the antidote acts to protect the packaging strain against the toxicity of doc.

The improvement in the present invention is that a non-replicative delivery system has an advantage in that once the phage coat has injected the nucleic acid into the targeted bacterium, the expression of the toxic agent or ribozyme will destroy the microbe, as opposed to a lytic infection cycle typical of an intact bacteriophage. Consequently, amplification of the phage coat will not be an issue and it is less likely that the non-replicative phage delivery system will generate an immune response such that subsequent use of the delivery system would be jeopardized. Moreover, if the patient has been exposed to a resistant pathogenic microbe and the therapeutic of the invention is effective and neutralizes the invading microbe, then it is expected that the microbial antigens liberated as a result of the action of the therapeutic, will illicit sufficient humoral immunity and cell-mediated immunity to confer protection against subsequent attacks.

5.9. Pharmaceutical Preparations/Formulations and Methods for Administration

A method of delivering a toxic agent or ribozyme to a target (e.g., a pathogen) in a subject is provided, comprising a) generating a liposome comprising a promoter and a sequence encoding a toxic agent or ribozyme; and b) delivering the liposome to the subject, whereby the target-specific promoter directs transcription of the toxic agent or ribozyme in the cells of the target. The target can be a pathogen, for example, a bacteria, fungus, yeast, parasite, virus or non-viral pathogen.

A method of targeted delivery of a toxic agent or ribozyme to a pathogen in a subject is provided, comprising a) generating a virion comprising non-viral DNA of the invention; b) combining it with a liposome; and b) delivering the liposome containing the virion to the subject, whereby liposome enters the eukaryotic cell and releases the virion, which delivers the DNA to the pathogen, whereby the pathogen-specific promoter directs transcription of the toxic agent or ribozyme in the cells of the pathogen.

A method of treating an infection in a subject is provided, comprising administering to the subject the liposome comprising DNA comprising a target-specific promoter and a sequence encoding a toxic agent or ribozyme, whereby the toxic agent or ribozyme encoded by the DNA is expressed and the infectious agent is killed or weakened. The liposome used in this method can comprise any ribozyme-encoding nucleic acid, or any toxic agent-encoding nucleic acid, particularly those described herein targeted to genes of the pathogen. The infection can be bacterial fungal, yeast, parasitic, viral or non-viral.

Parenteral administration, if used, is generally characterized by injection (intravenous, intradermal, subcutaneous and intramuscular). Injectables can be prepared in conventional forms, either as liquid solutions or suspensions, solid forms suitable for solution of or suspension in liquid prior to injection, or as emulsions. A more recently revised approach for parenteral administration involves use of a slow release or sustained release system such that a constant level of dosage is maintained. See, e.g. U.S. Pat. No. 3,610,795, which is incorporated by reference herein.

The present invention relates to prophylactic administration. For example, many hospital patients or immunocompromised hosts are particularly susceptible to pathogenic infections. Further, many hospital strains of pathogens are resistant to traditional antibiotic treatment, such as Penicillin. The therapeutics of the invention are particularly useful for preventing pathogenic infection or treating infections caused by resistant strains of pathogens.

Suitable carriers for parenteral administration of the substance in a sterile solution or suspension can include sterile saline that can contain additives, such as ethyl oleate or isopropyl myristate, and can be injected, for example, intravenously, as well as into subcutaneous or intramuscular tissues.

Topical administration can be by creams, gels, suppositories and the like. Ex vivo (extracorporeal) delivery can be as typically used in other contexts.

Oral administration is also provided. Suitable carriers for oral administration include one or more substances which can also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers can be water, pyrogen free saline, pharmaceutically accepted oils, or a mixture of any of these. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

The therapeutic of the invention can be administered to the subject in amounts sufficient to produce an antibiotic effect or to inhibit or reduce the activity of the target pathogen. Optimal dosages used will vary according to the individual, on the basis of age, size, weight, condition, etc, as well as the particular modulating effect being induced. One skilled in the art will realize that dosages are best optimized by the practicing physician and methods determining dosage are described, for example, in Remington's Pharmaceutical Sciences [Marti, E. W. (ed.) Remington's Pharmaceutical Sciences, latest edition Mack Publishing Co., Easton, Pa.]. Treatment can be at intervals and can be continued for an indefinite period of time, as indicated by monitoring of the signs, symptoms and clinical parameters associated with a particular infection. The parameters associated with infection are well known for many pathogens and can be routinely assessed during the course treatment.

6. EXAMPLE

Construction & Characterization of LEASHI Promoter

The present invention provides bacterial promoters that allow for tight regulation of transcription and enhanced expression. A novel promoter called LEASHI has been constructed from three elements (see FIG. 1A). The first element, termed RIP was a combination of two consensus sites at −10(TATAAT) and −35(TTGACA) located with respect to transcription initiation. The second element was based on the lacI repressor binding sequence (termed lac operator sequence) which was placed between the −10 and −35 consensus sites. Placement of the lac operator between the −10 and −35 sites, more effectively blocked RNA polymerase binding to the promoter, thus enhancing transcriptional control from the promoter. The promoter was designed such that it was 'switched on' following the addition of isopropyl B-D-thiogalacto pyranoside, which binds and subsequently titrates out the repressor protein. RNA polymerase can then bind to the promoter and transcription can proceed.

The third element of the LEASHI promoter was the UP element. The UP element was an adenine/thymine rich sequence which was placed immediately upstream of the −35 element. Addition of the UP element, further increased expression from this promoter.

The LEASHI promoter sequence: (SEQ ID NO:1)

5' GATCCTCAGAAAATTATTTTAAATTTC-
CAATTGACATT GTGAGCGGATAACAATATAAT-
GTGTGGA3'

A novel promoter called Modified rrnB has been constructed (see FIG. 1B). Modified rrnB promoter sequence: (SEQ ID NO:2)

5'AGAAAGCAAAAATAAATGCTTGACACTG-
TAGCGGGAAGGCGTATA ATGGAATTGT-
GAGCGGATAACAATTCACA 3'

Classical bacterial inducible promoters are renowned for their inability to tightly control transcription, and a significant level of background expression is characteristically observed. A significant advantage of the LEASHI promoter of the present invention is that it alleviates the high levels of background commonly observed in inducible promoters. A limiting factor leading to high background levels of transcription when a promoter of interest is on a high-copy number plasmid is due to the lack of repressor molecules available to bind to the promoters. The present invention overcomes this problem by using a lacI expression plasmid and secondly, by placement of the lac operator between the −35 and −10 consensus elements which more effectively blocks transcription during normal conditions. Furthermore, the UP element placed immediately upstream of the −35 region enhanced transcription from the promoter.

As described below, ribozymes of the invention has been operably linked to the LEASHI promoter. In another specific embodiment of the invention, a toxic agent of the invention was operably linked to a LEASHI promoter.

7. EXAMPLE

Effects of Doc, Gef, or DicF1 on Bacterial Growth

In order to demonstrate the methods of the invention, the inventors have expressed and targeted several toxic agents to bacterial pathogens. Toxic agents were selected based on their ability to inhibit the growth of a pathogen or diseased cell or cause lethality in a pathogen or diseased cell.

To illustrate that a toxic agent may be a toxic gene product of an addiction system toxic, a toxic gene product of a chromosomally endcoded toxin, or antisense molecule, virions containing doc, gef, or DicF1 nucleic acids were engineered into Transfer plasmids for used in the P1 bacteriophage delivery system. Plasmid construction was performed by standard methods known in the art. Plasmids containing the toxic agents doc or gef were also been engineered such that a ribosome entry site has been constructed upstream of the nucleic acids encoding the toxic agent in order to increase the levels of translation of doc or gef. Plasmids harboring a toxic agent was called a Transfer plasmid. The transfer plasmid was constructed such that it contained 1) an origin of replication 2) selectable marker 3) P1 PAC site, and PAC ABC genes 4) P1 lytic replicon 5) nucleic acids encoding the toxic agent (e.g., Doc, Gef, or DicF1).

A packaging strain (e.g., bacteria cell) was then used to package the Transfer plasmid containing Doc, Gef, or DicF1 into a bacteriophage phage head. The packaging strain for each of the three toxic agents contained the P1 bacteriophage prophage as well as the Transfer plasmid containing the nucleic acids encoding the toxic agent. In some cases, the packaging strain also contained a third plasmid, if necessary, which encoded additional antidote protein which acted to protect the packaging strain against the toxicity of the toxic agent or the third plasmid encoded additional repressor protein to switch off the promoter of the Transfer plasmid.

Thus, the packaging strain (P1 lysogen) was used to package the transfer plasmid containing the toxic agent (e.g., Doc, Gef, or DicF1) into phage heads or virions. Phage lysates of the packaging strain contained the infectious bacteriophage virions, and were used to infect bacterial targets in the following manner.

The P1 lysogen (Plcm C1.100) carrying the transfer plasmid with the toxic agent (Doc or Gef or DicF1) was grown at 30° C. in LB, 10 mM $MgSO_4$, 5 mM $CaCl_2$, 12.5µ/ml chloramphenicol unit $A_{450}$ reached 0.8 at which time the culture was shifted to a 42° C. water bath and aerated vigorously for 1 h. Chloroform was added and incubation continued for an additional 20 min at 37° C. The phage stock was clarified by centrifugation at 4,000 g for 20 min. DNase (1 µg/ml) and RNase (10 µg/ml) were added and after incubation at 37° C. 30 min the phage were centrifuged at 4,000 g 20 min. Phage particles were precipitated from the phage stocks by adding NaCl to 1 M and polyethylene glycol 6000 to 10% (w/v). After incubation on ice for 2 h the phage were pelleted by centrifugation at 11,000 g for 15 min. The pellet was carefully dissolved in 50 mM Tris.Cl pH 7.5, 10 mM $MgSO_4$, 5 mM $CaCl_2$, 0.01% Gelatin. Polyethylene glycol was removed by extraction's with chloroform.

The phage lysates were then used to infect a selected pathogen (e.g., *E. coli*). Target cells ($10^5$ CFU/ml, treated with 10 mM $MgSO_4$, 5 mM $CaCl_2$) were infected at various M.O.I s (0.1, 1, 10, 100) with each of the above phage lysate. Following 30 min infection at 30° C. Cell death was assessed by scoring the plates for the total number of colony forming units.

Results indicated that the infection of the bacterial cells with the phage lysates comprising the infectious virions containing a toxic agent was capable of killing the infected bacterial cells. Further, bacterial cell death was seen to be dose dependent such that higher M.O.I lead to increased cell death. Thus, the methods and compositions of the invention are useful as antimicrobial agents for treating pathogenic infections.

8. EXAMPLE

Construction & Characterization of Sof Sense RNA as a Toxic Agent

In order to demonstrate that a toxic agent may be delivered and expressed using a ribozyme cassette, the inventors have engineered a toxic agent directed against an essential molecule called Sof, and delivered the toxic agent in a ribozyme cassette to bacterial cells to cause the death of the bacterial cells.

As described herein above, a toxic agent may be a molecule which is designed to target an essential molecule of a pathogen or selected cell. An example of an essential antisense molecule for bacteria is Sof. Sof is an antisense antidote for a chromosomally encoded toxin called Gef. Sof normally acts to regulate the levels of Gef in the pathogen, and thus allows the cell to survive in the presence of Gef. The inventors of the present invention have designed sense molecules which are complementary to Sof. The sense molecules against Sof acted to inhibit the ability of Sof to regulate Gef, and thus caused toxicity in the pathogen by allowing the endogenous Gef levels to become toxic to the bacteria.

Specifically, Sof sense was constructed into a triple ribozyme cassette (with 5' and 3' cis-acting ribozymes). The ribozyme cassette containing the Sof sence toxic agent was linked to the LEASHI promoter. The nucleic acids encoding the ribozyme cassette were then used to transform *E. coli*. Bacterial cells were plated onto LB Amp+IPTG. Plates were incubated overnight at 37° C. Plates were then scored for the presence of transformants, size of colonies, growth rate, and morphological differences.

Results of these studies indicated that expression of the Sof sense molecules from the ribozyme cassette lead to toxic effects in the targeted bacteria.

9. EXAMPLE

Ribozymes and Ribozyme Cassettes

Figure 3:
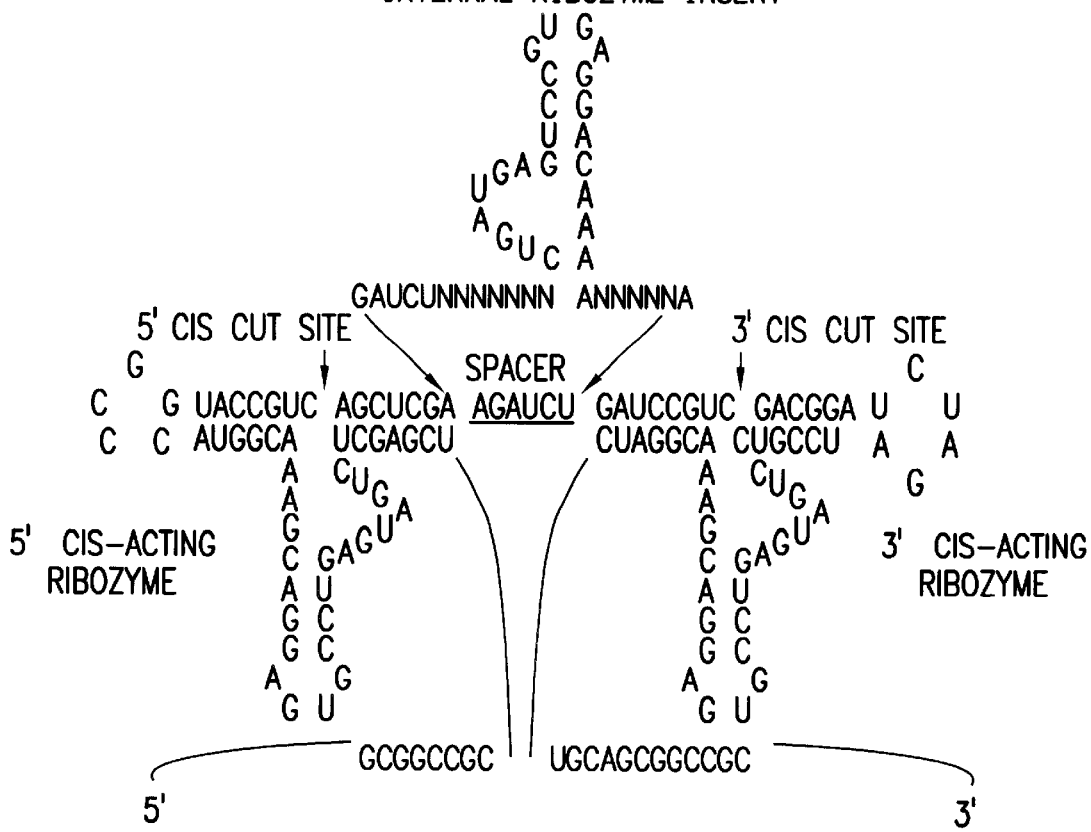

The ribozyme cassettes which are particularly useful in the methods of the invention include but are not limited to the following:

pClip (the genetic element described in FIG. 3) is a modification of pBluescript, wherein the cassette shown is dropped into the Not I site in pBluescript. The toxic agent or trans-acting ribozyme is constructed into the Bgl II site (TGCTCT). Liberation of internal ribozymes or toxic agents from pClip results in a distribution of the toxic agent or ribozyme(s) to approximately 20% nuclear and 80% cytoplasmic, when delivered to a eukaryotic cell. pClip is also used to target prokaryotic cells.

Figure 4:
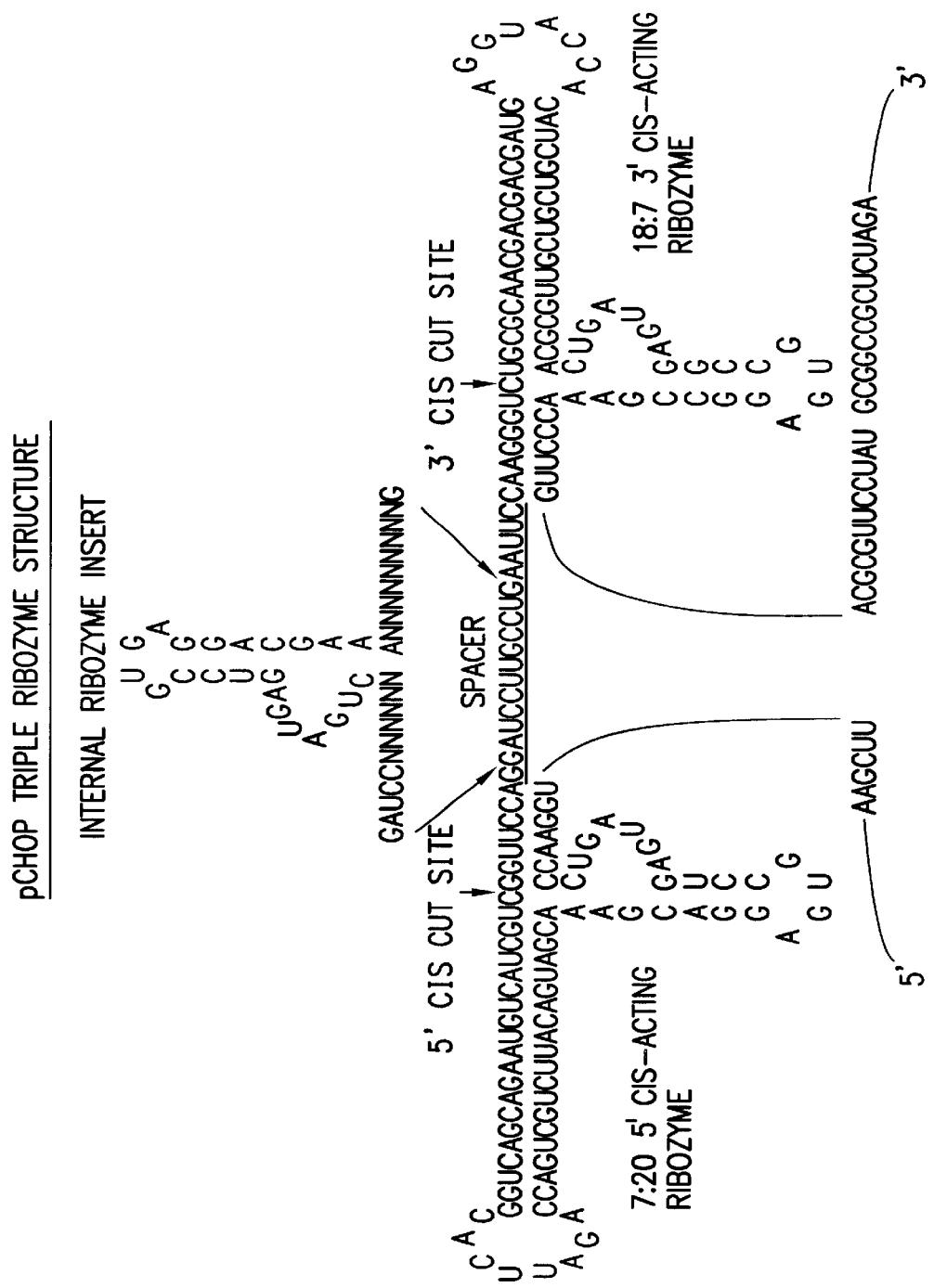

A second ribozyme cassette/vector that is useful in connection with the methods of the invention is pChop. pChop is modified from pClip to convey a more efficient and effective liberation of the internal trans-acting ribozymes or toxic agents. The pChop ribozyme cassette is diagramed in FIG. 4. Liberation of internal catalytic core ribozymes from pChop increases localization to the nucleus when delivered to a eukaryotic cell.

Figure 5:
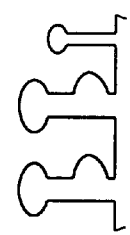
Figure 5:
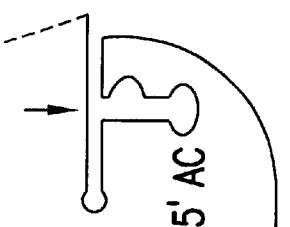
Figure 5:
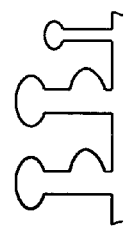
Figure 5:
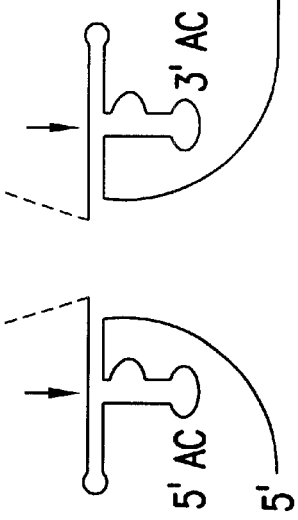

A third ribozyme cassette that was useful in connection with the methods of the invention is pSnip. The pSnip multi-ribozyme is constructed by engineering the pClip cassette 5' to pChop. In addition, the pSnip multi-ribozyme contains catalytic core sequences with two trans-acting ribozymes or toxic agents in each cassette. Each pair of trans-acting ribozymes or toxic agents is linked by a short spacer and stabilized by a hairpin loop located 3' to the pair. FIG. 5 diagrams the schematic of the pSnip cassette.

A trans-acting ribozyme, or antisense toxic agent is synthesized as reverse complementary overlapping oligodeoxynucleotides, which are designed in such a way that when annealed they form single stranded ends identical to those produced by digestion with the restriction endonuclease contained with the region between the two cis-acting ribozymes. In this particular example the restriction endonuclease recognition site is that recognized by Bgl II. Essentially any RNA can be targeted: specificity is conferred by selecting sequences for the ribozyme that are reverse and complementary to sequences flanking the chosen cleavage site in the targeted RNA molecule. The toxic agent(s) or trans-acting ribozymes are then cloned into the cloning region (polylinker) within the double ribozyme cassette to produce the targeted toxic agent or ribozyme. Trans-acting ribozymes targeted to prokaryotic sequences have been constructed including, but not limited to, *Escherichia coli*: secA (EcosecA, AE000119 U00096), gene X (EcosecA, AE000119 U00096) ftsZ (AE000119;U00096), dnaG (AE000388 U00096), rpoA (AE000407 U00096) and tRNA-asp (X14007), *Streptomyces lividins* secA (Z50195), *Enterococcus faecalis*, ftsZ (U94707) *Pseudomonas putida*, dnaG (185774), *Streptomyces coelicolor* rpoA (X92107), *Staphylococcus warneri* tRNA-Asp (X66089 S42075), Staphloccocus RNA III.

The utility of the design using eukaryotic sequences has also been evaluated; a) repetitive B2 transcripts (B2); b) RNA polymerase I (polI); c) Hepatitis B virus (HBV); d) Sonic Hedgehog (SH); e) Human Papillomavirus E6/E7 protein (HPV); f) RNA polymerase II (polII); g) Insulin-like Growth Factor 1 (IGF1); h) retinoblastoma protein (RB); i) and j) Multicatalytic Proteinase alpha-subunits C3 and C9 (C3 and C9, respectively); k) telomerase (tel); l) Transforming growth factor beta (TGFβ); m) catalase (CAT); n) Peroxisome proliferation associated receptor (PpaRα); and o) Cytochrome $P_{450}$ 1E1 (p4501E1). Target RNAs (with locus names and accession numbers) as well as the selected target sites are presented (Table 1).

TABLE 1

Summary of Targeted RNAs and Target Sites.

| Target RNA | EMBL Locus | Accession | Target Site | Functional Testing in vitro | Functional Testing in vivo |
|---|---|---|---|---|---|
| pol II | HSRNAP14K | Z27113 | $GTC_{83}$ | ND | ND |
| HBV | XXHEPAV | X02496 | $GTC_{438}$ | IP | + |
| RB | MUSP105RB | M26391 | $GTC_{264}$ | + | + |
| IGF1 | HUMIGF1B | M37484 | $GTC_{185}$ | ND | ND |
| SH | MMEVX1 | X54239 | $GTC_{558}$ | IP | IP |
| Pol I | MUSRPA40 | D31966 | $GTC_{458}$ | + | + |
| HPV | PPH16 | K02718 | $GTT_{108}$ | IP | + |
| C3 | RATC3AA | J02897 | $GTT_{22}$ | + | + |
| C9 | RNPTSC9 | X533304 | $GTC_{101}$ | + | + |
| B2 | B2-Consensus | ## | $GTT_{24}$ | + | + |
| Tel | MMU33831 | U33B31 | $CTA_{63}$ | ND | ND |

10. EXAMPLE

Delivery and in vivo Testing

Biologic Delivery

The toxic agents and/or ribozymes of the present invention may be delivered by a wide variety of viral vectors and bacteriophage as described herein.

In one embodiment of the invention, a toxic agent is encoded in a Transfer plasmid, and is used in connection with a P1 bacteriophage delivery system. Such Transfer plasmid preferably contains 1) an origin or replication 2) selectable marker 3) P1 PAC site and PAC ABC genes 4) P1 lytic replicon 5) nucleic acids encoding one or more toxic agents of the invention (e.g., antisense molecule, ribozyme, or toxic protein, etc). In a preferred embodiment of the invention, the bacteriophage P1 prophage (P1 plasmid) is engineered such that viral DNA can not be packaged into virions, such as, for example, by deletion of the PAC site from the P1 plasmid.

In another embodiment, the toxic agents and/or ribozymes may be delivered via a plasmid encoding the toxic agents and/or ribozymes, a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of replication on the plasmid and all of the structural components needed to form mature virions; however, the lysogen is not able to replicate and package its own DNA into the virions. The lysogen also carries the $cI^{857}$ temperature-sensitive repressor mutation. Induction of the lysogen by temperature shift to 42° C. or by other means, such as exposure to 5 J/m2 of ultraviolet radiation will mobilize the plasmid and result in its replication and packaging into lambda virions. The virions can then be harvested, purified free of *E. coli* proteins and be used to deliver the toxic agents and/or ribozyme gene(s) to *E. coli*. Similar methods are performed for *Pseudomonas aerugunosa* in order to deliver a toxic agent and/or ribozyme to *P. aerugunosa*.

Abiologic Delivery

Abiologic delivery of the toxic agent and/or ribozymes is accomplished with constructs that have been engineered to be expressed within the targeted tissue or pathogen. Briefly, the genetic element containing the promoter and the toxic agent and/or ribozyme(s) are complexed with cationic liposomes (Lipofectamine—Gibco BRL) in a 1:10 ratio and are introduced into test animals by either single or multiple injection of 0.2 ml total volume nucleic acid-liposome mixture.

In vivo Testing

Following the demonstration that toxic agents and/or ribozymes of the present invention have an in vitro biological activity (either directly on bacterial cultures or in an infectious tissue culture cell assay system), the effectiveness of the toxic agents and/or ribozymes, is shown in an in vivo model system. To demonstrate the efficacy of toxic agents and/or ribozymes of the invention in vivo, experimental animal model systems are utilized. For an initial demonstration of the efficacy of the toxic agents and/or ribozymes in vivo, mice are infected with a microbial pathogen which has previously been shown to be sensitive to the toxic agents and/or ribozymes construct(s) and the effect of toxic agents and/or ribozymes administered in vivo is determined. In the first series of in vivo trials, one determines the effectiveness of toxic agents and/or ribozymes at preventing an acute infection in a murine model system when the toxic agents and/or ribozymes is added directly to the microbe prior to administration in vivo.

The next series of trials determine whether the administration of toxic agents and/or ribozymes after infection is effective at preventing an acute bacterial infections. In addition to the clinical status of infected mice, tissues obtained at necropsy are examined histologically and the presence of replicating microorganism in tissue samples is determined by standard methodology. Animals can be infected by various routes (systemic and/or mucosal) and the toxic agents and/or ribozymes are delivered over time after infection by systemic, mucosal, or topical routes. Both abiologic as well as biological delivery of the toxic agents and/or ribozymes is used. The demonstration of a positive effect of the toxic agents and/or ribozymes in controlled experimental model system provides compelling evidence for the efficacy of the preparation and determines whether or not the preparation warrants evaluation under conditions of standard clinical trials.

Throughout this application various publications are referenced. The disclosures of these publications in their entireties are hereby incorporated by reference into this application in order to more fully describe the state of the art to which this invention pertains.

What is claimed is:

1. A recombinant nucleic acid comprising a nucleotide sequence encoding one or more antisense RNA operably linked to a pathogen-specific or tissue-specific promoter, wherein the antisense RNA comprises the sequence of DicF1, as presented in FIG. 2 (SEQ ID NO:3).

2. A recombinant nucleic acid comprising a nucleotide sequence encoding one or more toxic agents operably linked to a pathogen-specific or tissue-specific promoter, wherein the promoter is the LEASHI promoter (as presented in FIG. 1A, SEQ ID NO:1).

3. A recombinant nucleic acid comprising a nucleotide sequence encoding one or more toxic agents operably linked to a pathogen-specific or tissue-specific promoter, wherein the toxic agent is constructed into a sequence encoding a ribozyme cassette comprising one or more autocatalytically cleaving ribozyme sequence, and wherein the ribozyme cassette is pChop.

4. A recombinant nucleic acid comprising a nucleotide sequence encoding one or more toxic agents operably linked to a pathogen-specific or tissue-specific promoter, wherein the toxic agent is constructed into a sequence encoding a ribozyme cassette comprising one or more autocatalytically cleaving ribozyme sequence, and wherein the ribozyme cassette is pSnip.

5. A recombinant nucleic acid comprising a nucleotide sequence encoding one or more toxic agents operably linked to a pathogen-specific or tissue-specific promoter, wherein the toxic agent is constructed into a sequence encoding a ribozyme cassette comprising one or more autocatalytically cleaving ribozyme sequence, and wherein the ribozyme cassette is pClip.

6. A nucleic acid comprising the nucleotide sequence of the LEASHI promoter, as presented in FIG. 1B (SEQ ID NO.1).

7. A nucleic acid comprising the nucleotide sequence of DicF1, as presented in FIG. 2 (SEQ ID NO:3).

8. A recombinant nucleic acid comprising a nucleotide sequence encoding one or more toxic agents operably linked to a pathogen-specific or tissue-specific promoter, wherein the promoter is a modified rrnB promoter (as presented in FIG. 1B, SEQ ID NO:2).

* * * * *

SEQUENCE LISTING

<160> NUMBER OF SEQ ID NOS: 7

<210> SEQ ID NO 1
<211> LENGTH: 65
<212> TYPE: DNA
<213> ORGANISM: Artificial Sequence
<220> FEATURE:
<223> OTHER INFORMATION: Description of Artificial Sequence: Promoter

<400> SEQUENCE: 1
gatctcagaa aattatttta aatttccaat tgacattgtg agcggataac aatataatgt    60
gtgga                                                               65

<210> SEQ ID NO 2
<211> LENGTH: 74
<212> TYPE: DNA
<213> ORGANISM: Artificial Sequence
<220> FEATURE:
<223> OTHER INFORMATION: Description of Artificial Sequence: Promoter

<400> SEQUENCE: 2
agaaagcaaa aataaatgct tgacactgta gcgggaaggc gtataatgga attgtgagcg    60
gataacaatt caca                                                     74

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: dicF1

<400> SEQUENCE: 3
caggcgacag gtatagtttc tctccgattt gtgcctgtcg cctgc                   45

<210> SEQ ID NO 4
<211> LENGTH: 135
<212> TYPE: RNA
<213> ORGANISM: Artificial Sequence
<220> FEATURE:
<223> OTHER INFORMATION: Description of Artificial Sequence: Ribosyme

<400> SEQUENCE: 4
gcggccgcuc gagcucugau gaguccguga ggacgaaacg guacccggua ccgucagcuc    60
gaagaucuga uccgucgacg gaucuagauc cguccugaug aguccgugag gacgaaacgg   120
aucugcagcg gccgc                                                   135

<210> SEQ ID NO 5
<211> LENGTH: 41
<212> TYPE: RNA
<213> ORGANISM: Artificial Sequence
<220> FEATURE:
<223> OTHER INFORMATION: Description of Artificial Sequence: Ribosyme
<220> FEATURE:
<221> NAME/KEY: modified_base
<222> LOCATION: (all "n" positions)
<223> OTHER INFORMATION: n=a,c,g,u

<400> SEQUENCE: 5
gaucunnnnn nncugaugag uccgugagga cgaaannnnn a                       41

<210> SEQ ID NO 6
<211> LENGTH: 218

```
<212> TYPE: DNA
<213> ORGANISM: Artificial Sequence
<220> FEATURE:
<223> OTHER INFORMATION: Description of Combined DNA/RNA Molecule:
      ribosyme
<220> FEATURE:
<223> OTHER INFORMATION: Description of Artificial Sequence: Ribosyme

<400> SEQUENCE: 6
aagcuuugga acccugauga guccgugagg acgaaacgau gacauucugc ugaccagauu        60
cacggucagc aagaauguca ucgucgguuc caggauccuu gccugaauuc caagggucug       120
cgcaacgacg acgaugaggu accacaucgu cgucguugcg cacugaugag gccgugaggc       180
cgaaacccuu ugacgcguuc cuaugcggcc gcucuaga                              218

<210> SEQ ID NO 7
<211> LENGTH: 44
<212> TYPE: RNA
<213> ORGANISM: Artificial Sequence
<220> FEATURE:
<223> OTHER INFORMATION: Description of Artificial Sequence: Ribosyme
<220> FEATURE:
<221> NAME/KEY: modified_base
<222> LOCATION: (all "n" positions)
<223> OTHER INFORMATION: n=a,c,g,u

<400> SEQUENCE: 7
gauccnnnnn ncugaugagu ccgugaggac gaaannnnnn nnng                        44
```